(12) United States Patent
Miller et al.

(10) Patent No.: US 10,370,351 B2
(45) Date of Patent: Aug. 6, 2019

(54) PHOTOINDUCED ELECTRON TRANSFER VOLTAGE-SENSITIVE COMPOUNDS

(71) Applicant: The Regents of the University of California, Oakland, CA (US)

(72) Inventors: Evan W. Miller, Berkeley, CA (US); Rishikesh Upendra Kulkarni, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/496,897

(22) Filed: Apr. 25, 2017

(65) Prior Publication Data

US 2017/0320846 A1    Nov. 9, 2017

Related U.S. Application Data

(60) Provisional application No. 62/327,433, filed on Apr. 25, 2016.

(51) Int. Cl.
*C07D 311/82* (2006.01)
*C07D 219/04* (2006.01)
*G01N 21/64* (2006.01)
*G01N 33/542* (2006.01)
*G01N 33/50* (2006.01)

(52) U.S. Cl.
CPC .......... *C07D 311/82* (2013.01); *C07D 219/04* (2013.01); *G01N 21/6428* (2013.01); *G01N 33/502* (2013.01); *G01N 33/5008* (2013.01); *G01N 33/542* (2013.01); *G01N 2500/10* (2013.01)

(58) Field of Classification Search
CPC combination set(s) only.
See application file for complete search history.

(56) References Cited

U.S. PATENT DOCUMENTS 9,651,494 B2 *   5/2017   Miller ................ G01N 33/5008

\* cited by examiner

*Primary Examiner* — Monique R Peets
(74) *Attorney, Agent, or Firm* — Gavrilovich, Dodd & Lindsey LLP

(57) ABSTRACT

The disclosure provides methods to synthesize photoinduced electron transfer voltage-sensitive compounds, the compounds made therefrom, and uses of the compounds thereof.

15 Claims, 17 Drawing Sheets

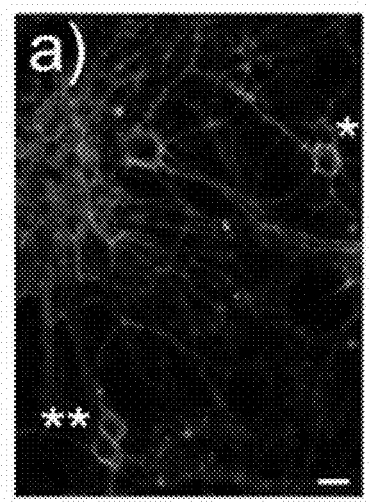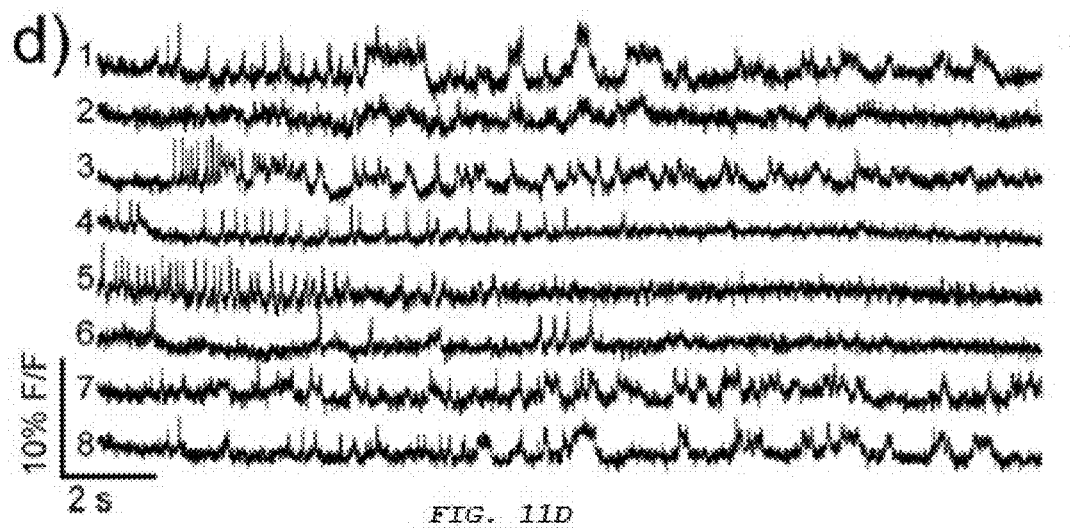
FIG. 11A
FIG. 11B
FIG. 11C
FIG. 11D

PHOTOINDUCED ELECTRON TRANSFER VOLTAGE-SENSITIVE COMPOUNDS

CROSS REFERENCE TO RELATED APPLICATIONS

This application claims priority under 35 U.S.C. § 119 from Provisional Application Ser. No. 62/327,433, filed Apr. 25, 2016, the disclosure of which is incorporated herein by reference.

STATEMENT AS TO FEDERALLY SPONSORED RESEARCH

This invention was made with Government support under Grant No. NS078561, awarded by the National Institutes of Health. The Government has certain rights in the invention.

TECHNICAL FIELD

The disclosure provides methods to synthesize photoinduced electron transfer voltage-sensitive compounds, the compounds made therefrom, and uses of the compounds thereof.

BACKGROUND

The development of fluorescent indicators for biological analytes has revolutionized the ability to interrogate biochemistry and biophysics in living cells.

SUMMARY

The disclosure provides for disclosure provides for photoinduced electron transfer voltage-sensitive compounds and uses thereof. The disclosure further provides methods to synthesize said photoinduced electron transfer voltage-sensitive compounds by introducing two sulfonic acid derivatives so as to force a molecular wire voltage sensor to adopt a perpendicular confirmation in the plasma membrane, thus increasing its voltage sensitivity. The compounds of the disclosure are useful as reagents for studying membrane potentials in excitable cells (e.g., neurons and cardiomyocytes) and non-excitable cells (e.g., epithelium, immune or other somatic cells). Moreover, the compounds of the disclosure are ideally suited for use in drug screening, neurobiology and basic science research.

In a particular embodiment, the disclosure provides for a compound comprising the structure of Formula II:

Formula II

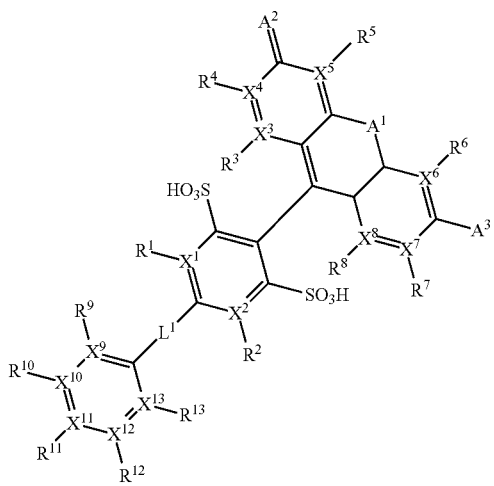

Wherein, $L^1$ is selected from the group consisting of:

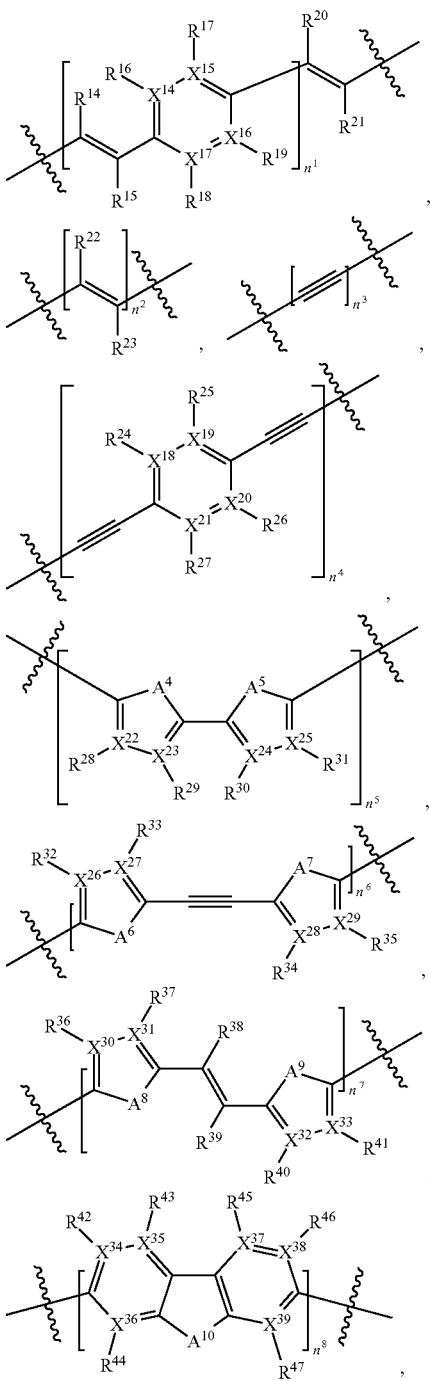

and any combination of the foregoing; $A^1$, $A^4$-$A^{10}$ are each independently selected from $CH_2$, CHR', $CR'_2$, NH, O, S, Se, Te, $SiH_2$, SiHR', $SiR'_2$, $GeH_2$, GeHR', $GeR'_2$, $SnH_2$, SnHR', $SnR'_2$, $PbH_2$, PbHR', or $PbHR'_2$, wherein R' is selected from the group consisting of D, optionally substituted FG, optionally substituted ($C_1$-$C_{12}$)alkyl, optionally substituted ($C_2$-$C_{10}$)heteroalkyl, optionally substituted ($C_1$-$C_{12}$)alkenyl, optionally substituted ($C_2$-$C_{10}$)heteroalkenyl, optionally substituted ($C_1$-$C_{12}$)alkynyl, and optionally substituted ($C_2$-$C_{10}$)heteroalkynyl; $A^2$ is selected from $NH_2$, S or O; $A^3$ is selected from $NH_2$, OH, SH and methoxy;

$X^1$-$X^{39}$ are independently selected from N or C, wherein when an X group is an N, then the R group is absent; and $R^1$-$R^{47}$ are independently selected from H, D, optionally substituted FG, optionally substituted ($C_1$-$C_{12}$) alkyl, optionally substituted ($C_2$-$C_{10}$)heteroalkyl, optionally substituted ($C_1$-$C_{12}$)alkenyl, optionally substituted ($C_2$-$C_{10}$)heteroalkenyl, optionally substituted ($C_1$-$C_{12}$)alkynyl, optionally substituted ($C_2$-$C_{10}$)heteroalkynyl, optionally substituted ($C_3$-$C_{12}$)cycloalkyl, optionally substituted ($C_5$-$C_{12}$)cycloalkenyl, optionally substituted aryl, optionally substituted heterocycle, optionally substituted mixed ring system, wherein one or more adjacent R groups can be linked together to form one or more substituted rings selected from the group comprising ($C_3$-$C_{12}$)cycloalkyl, ($C_3$-$C_{12}$)cycloalkenyl, heterocycle, aryl, and mixed ring system; and $n^1$-$n^8$ are independently an integer selected from 0 to 10.

In another embodiment, the disclosure provides for a compound which comprises the structure of Formula III:

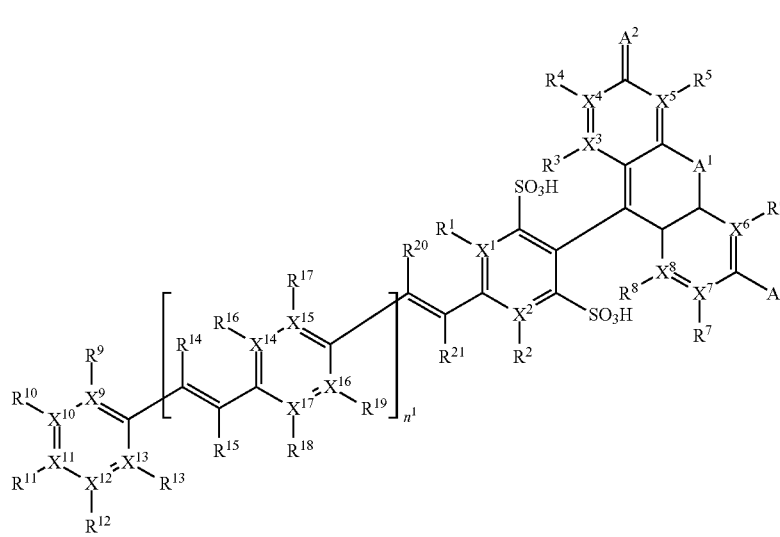

Formula III wherein, $A^1$ is selected from $CH_2$, CHR', $CR'_2$, NH, O, S, Se, Te, $SiH_2$, SiHR', $SiR'_2$, $GeH_2$, GeHR', $GeR'_2$, $SnH_2$, SnHR', $SnR'_2$, $PbH_2$, PbHR', or $PbHR'_2$, wherein R' is selected from the group consisting of D, optionally substituted FG, optionally substituted ($C_1$-$C_{12}$)alkyl, optionally substituted ($C_2$-$C_{10}$)heteroalkyl, optionally substituted ($C_1$-$C_{12}$)alkenyl, optionally substituted ($C_2$-$C_{10}$) heteroalkenyl, optionally substituted ($C_1$-$C_{12}$)alkynyl, and optionally substituted ($C_2$-$C_{10}$)heteroalkynyl; $A^2$ is $NH_2$ or O; $A^3$ is selected from $NH_2$, OH and methoxy; $X^1$-$X^{17}$ are independently selected from N or C, wherein when an X group is an N, then the R group is absent; and $R^1$-$R^{21}$ are independently selected from H, D, optionally substituted FG, optionally substituted ($C_1$-$C_{12}$) alkyl, optionally substituted ($C_2$-$C_{10}$)heteroalkyl, optionally substituted ($C_1$-$C_{12}$)alkenyl, optionally substituted ($C_2$-$C_{10}$) heteroalkenyl, optionally substituted ($C_1$-$C_{12}$) alkynyl, optionally substituted ($C_2$-$C_{10}$) heteroalkynyl, optionally substituted ($C_3$-$C_{12}$)cycloalkyl, optionally substituted ($C_5$-$C_{12}$)cycloalkenyl, optionally substituted aryl, optionally substituted heterocycle, optionally substituted mixed ring system, wherein one or more adjacent R groups can be linked together to form one or more substituted rings selected from the group comprising ($C_3$-$C_{12}$)cycloalkyl, ($C_3$-$C_{12}$)cycloalkenyl, heterocycle, aryl, and mixed ring system; and $n^1$ is an integer selected from 0 to 10.

In a further embodiment, the disclosure provides for a compound which comprises the structure of Formula III(a):

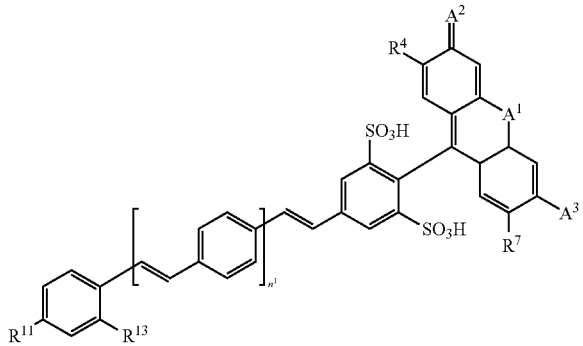

Formula III(a)

wherein, $A^1$ is selected from $CH_2$, CHR', $CR'_2$, NH, O, S, Se, Te, $SiH_2$, SiHR', $SiR'_2$, $GeH_2$, GeHR', $GeR'_2$, $SnH_2$, SnHR', $SnR'_2$, $PbH_2$, PbHR', or $PbHR'_2$, wherein R' is selected from the group consisting of D, optionally substituted FG, optionally substituted ($C_1$-$C_6$) alkyl, optionally substituted ($C_2$-$C_5$) heteroalkyl, optionally substituted ($C_1$-$C_6$) alkenyl, optionally substituted ($C_2$-$C_5$)heteroalkenyl, optionally substituted ($C_1$-$C_6$)alkynyl, and optionally substituted ($C_2$-$C_5$)heteroalkynyl; $A^2$ is $NH_2$ or O; $A^3$ is $NH_2$ or OH; $R^4$ and $R^7$ are independently selected from H, F, and Cl; $R^{11}$ is selected from $NH_2$, NH($R^{50}$), N($R^{50}$)$_2$, wherein $R^{50}$ is a ($C_1$-$C_3$) alkyl; $R^{13}$ is selected from H, CN, alkoxy, OH, halo and amino; and $n^1$ is an integer selected from 0 to 5.

In yet a further embodiment, the disclosure provides for a compound which comprises the structure of Formula III(b):

Formula III(b)

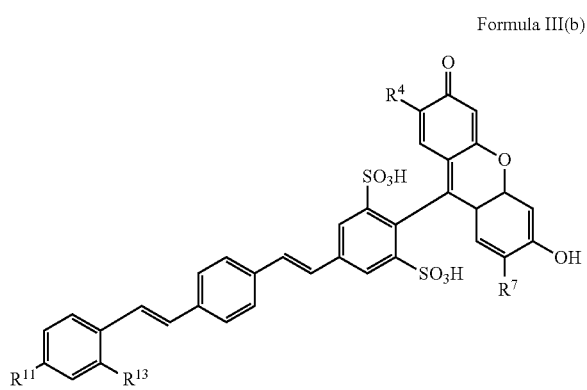

wherein, $R^4$ and $R^7$ are selected from H, F, and Cl; $R_{11}$ is selected from $NH_2$, $NH(R^{50})$, $N(R^{50})_2$, wherein $R^{50}$ is a $(C_1$-$C_3)$alkyl; and $R^{13}$ is H or a methoxy.

In a certain embodiment, a compound of the disclosure has one or more of the following characteristics: the compound is water soluble; the compound exhibits a tilt angle of about 0°; the compound exhibits a voltage sensitivity of 63% ΔF/F per 100 mV or greater; and the compound can undergo photoinduced electron transfer. In a further embodiment, the compound is characterized by being water soluble; exhibits a tilt angle from 0° to 20°; exhibits a voltage sensitivity of 63% ΔF/F per 100 mV or greater; and can undergo photoinduced electron transfer.

In another embodiment, the disclosure also provides a method to image cells, comprising: contacting the cell with a compound of any preceding claim; illuminating the cells with light having a first wavelength; imaging the cells by detecting light having a second wavelength, wherein the first wavelength and second wavelength of light have different wavelengths, and wherein the light having the second wavelength is in the far red to near infrared region. In yet another embodiment, the method further comprises: contacting the cells with one or more additional optogenetic tools; and imaging the cells be detecting light emissions at one or more additional wavelengths. Examples of optogenetic tools include, but are not limited to, GFP, $Ca^{2+}$ indicators, voltage sensors based on cpGFP, and ChannelRhodopsin2 (ChR2).

In another embodiment, the disclosure further provides a method to measure changes in membrane potential in an excitable cell comprising: contacting the excitable cell with a compound of the disclosure; stimulating the cell to evoke action potentials; and measuring action potential firing by optical or electrical sampling. In a further embodiment, the optical sampling is measured using an electron multiplying charge couple device. In yet a further embodiment, the excitable cell is stimulated using a whole-cell current clamp or by field stimulation. Examples of excitable cells include, but are not limited to, neuron, cardiomyocyte, myocyte, or a secretory cell. In another embodiment, the method interrogates membrane potentials of a neuron.

In a particular embodiment, the disclosure provides a kit comprising: a plurality of aliquots which comprise a compound disclosed herein in a buffered solution, or a concentrated solution comprising a compound disclosed herein in a buffered solution that is subsequently diluted prior to use.

In another embodiment, the disclosure provides a method to produce a compound of the disclosure using the methods and schemes as shown and described in the specification and figures.

In yet another, the disclosure further provides for a compound as substantially shown and described in the specification and figures.

DESCRIPTION OF DRAWINGS

FIG. 11A-D shows imaging membrane potential changes in cultured rat hippocampal neurons and hPSC-derived midbrain dopaminergic (mDA) neurons using dsVF2.2 (OMe).Cl. (A) Confocal images of rat hippocampal neurons stained with 500 nM dsVF2.2(OMe).Cl. * and ** are zoomed regions of the indicated neurons (B) Transmitted light image (DIC) of hPSC-derived mDA neurons. (C) Widefield fluorescence image of mDA neurons from panel b stained with 500 nM dsVF2.2(OMe).Cl. (D) Fractional change in fluroescence vs. time for cells indicated in panels b. Each trace represents the fluorescence intensity from the indicated cell; all traces have been bleach corrected and are unfiltered. Scale bars are 20 μm.

DETAILED DESCRIPTION

Figure 1A:
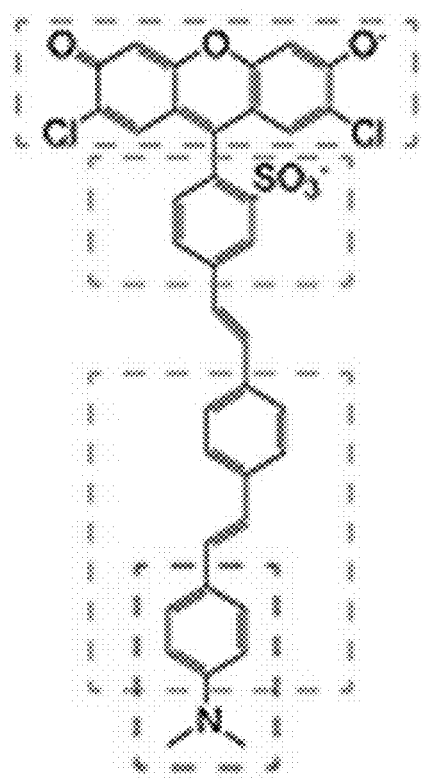
FIG. 1A-C shows parameterization of the msVF molecule in CHARMM general force field. (A) Division of msVF into four parts: xanthene derivative, benzenesulfonate, (E)-stilbene, and N,N-dimethylaniline. (B) Interaction energy calculation between atoms on the xanthene derivative and a TIP3p water. The calculation was performed at the MP2/6-31G* level for the two chlorine atoms and at the HF/6-31G* level for the remaining ones. Due to the symmetry of the compound, calculation was only performed on half of the atoms. (C) Optimization of the dihedral OG312-CG2R61-CG2R61-CLGR1 through potential energy scan performed via fftk and Gaussian 09.

As used herein and in the appended claims, the singular forms "a," "an," and "the" include plural referents unless the context clearly dictates otherwise. Thus, for example, reference to "a molecular wire" includes a plurality of such molecular wires and reference to "the VF dyes" includes reference to one or more VF dyes and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood by one of ordinary skill in the art to which this disclosure belongs. Although many methods and reagents similar to or equivalent to those described herein can be used in the practice of the disclosed methods and compositions, the exemplary methods and materials are now described.

The term "alkyl", refers to an organic group that is comprised of carbon and hydrogen atoms that contain single covalent bonds between carbons. Typically, an "alkyl" as used in this disclosure, refers to an organic group that contains 1 to 30 carbon atoms, unless stated otherwise. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkenyl", refers to an organic group that is comprised of carbon and hydrogen atoms that contains at least one double covalent bond between two carbons. Typically, an "alkenyl" as used in this disclosure, refers to organic group that contains 1 to 30 carbon atoms, unless stated otherwise. While a $C_1$-alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains 1 to 30 carbon atoms, unless stated otherwise. While a $C_1$-alkynyl can form a triple bond to a carbon of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "cylcloalkyl", as used in this disclosure, refers to an alkyl that contains at least 3 carbon atoms but no more than 12 carbon atoms connected so that it forms a ring. A "cycloalkyl" for the purposes of this disclosure encompass from 1 to 12 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "cylcloalkenyl", as used in this disclosure, refers to an alkene that contains at least 3 carbon atoms but no more than 12 carbon atoms connected so that it forms a ring. A "cycloalkenyl" for the purposes of this disclosure encompass from 1 to 12 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

The term "aryl", as used in this disclosure, refers to a conjugated planar ring system with delocalized pi electron clouds that contain only carbon as ring atoms. An "aryl" for the purposes of this disclosure encompass from 1 to 12 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term "heterocycle", as used in this disclosure, refers to ring structures that contain at least 1 noncarbon ring atom. A "heterocycle" for the purposes of this disclosure encompass from 1 to 12 heterocycle rings wherein when the heterocycle is greater than 1 ring the heterocycle rings are joined so that they are linked, fused, or a combination thereof. A heterocycle may be a hetero-aryl or nonaromatic, or in the case of more than one heterocycle ring, one or more rings may be nonaromatic, one or more rings may be hetero-aryls, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O.

The term "mixed ring system" refers to optionally substituted ring structures that contain at least two rings, and wherein the rings are joined together by linking, fusing, or a combination thereof. A mixed ring system comprises a combination of different ring types, including cycloalkyl, cycloalkenyl, aryl, and heterocycle.

The term "unsubstituted" with respect to hydrocarbons, heterocycles, and the like, refers to structures wherein the parent chain contains no substituents.

The term "substituted" with respect to hydrocarbons, heterocycles, and the like, refers to structures wherein the parent chain contains one or more substituents.

The term "substituent" refers to an atom or group of atoms substituted in place of a hydrogen atom. For purposes of this disclosure, a substituent would include deuterium atoms.

The term "hydrocarbons" refers to groups of atoms that contain only carbon and hydrogen. Examples of hydrocarbons that can be used in this disclosure include, but are not limited to, alkanes, alkenes, alkynes, arenes, and benzyls.

The term "functional group" or "FG" refers to specific groups of atoms within molecules that are responsible for the characteristic chemical reactions of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Examples of FG that can be used in this disclosure, include, but are not limited to, substituted or unsubstituted alkyls, substituted or unsubstituted alkenyls, substituted or unsubstituted alkynyls, substituted or unsubstituted aryls, substituted or unsubstituted hetero-alkyls, substituted or unsubstituted hetero-alkenyls, substituted or unsubstituted hetero-alkynyls, substituted or unsubstituted cycloalkyls, substituted or unsubstituted cycloalkenyls, substituted or unsubstituted hetero-aryls, substituted or unsubstituted heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $SO_3H$, $Si(OH)_3$, $Ge(OH)_3$, $Sn(OH)_3$, $Si(SH)_4$, $Ge(SH)_4$, $Sn(SH)_4$, $AsO_3H$, $AsO_4H$, $P(SH)_3$, $SO_2$, $SO_3^-$ and $As(SH)_3$.

As used herein, a wavy line intersecting another line that is connected to an atom indicates that this atom is covalently bonded to another entity that is present but not being depicted in the structure. A wavy line that does not intersect a line but is connected to an atom indicates that this atom is interacting with another atom by a bond or some other type of identifiable association.

All publications mentioned herein are incorporated herein by reference in their entirety for the purposes of describing and disclosing methodologies that might be used in connection with the description herein. Moreover, with respect to any term that is presented in the publications that is similar to, or identical with, a term that has been expressly defined in this disclosure, the definition of the term as expressly provided in this disclosure will control in all respects.

Traditional methods to measure membrane potential rely on invasive electrodes, introduced via pipette or on micro or nano-arrays. Voltage imaging with fluorescent probes is an attractive solution because voltage imaging circumvents problems of low-throughput, low spatial resolution, and high invasiveness associated with more traditional electrode-based techniques. Provided herein are alternatives to the traditional methods of measuring membrane potentials. In particular, the disclosure provides chemical indicators for sensing a membrane potential. These chemical indicators of the disclosure allow for studies on membrane voltage, not only in excitable cells, such as neurons and cardiomyocytes, but also in non-excitable cells found in the rest of the body.

Provided herein are compounds that can be used for voltage imaging via a photoinduced electron transfer (PeT) quenching mechanism to directly image transmembrane voltage changes. Previously reported voltage-sensitive fluorescent (VF) dyes have proven useful in a number of imaging contexts. However, a rational design scheme for synthesizing VF dyes remains elusive, due in part to the incomplete understanding of the biophysical properties influencing voltage sensitivity.

The compounds disclosed herein sense voltage via a PeT-based mechanism where the transmembrane potential of the cell strongly influences the rate of PeT; at hyperpolarizing, or negative, potentials, PeT is accelerated and fluorescence is quenched. At depolarizing, or positive, voltages, fluorescence increases as the rate of PeT decreases. It has been proposed that he magnitude of the molecular Stark effect, or perturbation of the chromophore orbital energies, is proportional to equation 1:

$$\Delta G = qr \cdot E \quad \text{(Eq. 1)}$$

where $\Delta G$ represents the change in energy associated with the shift in wavelength, q is the effective charge transferred, r is the distance that quantity q travels and E is the electric field.

Figure 3A:
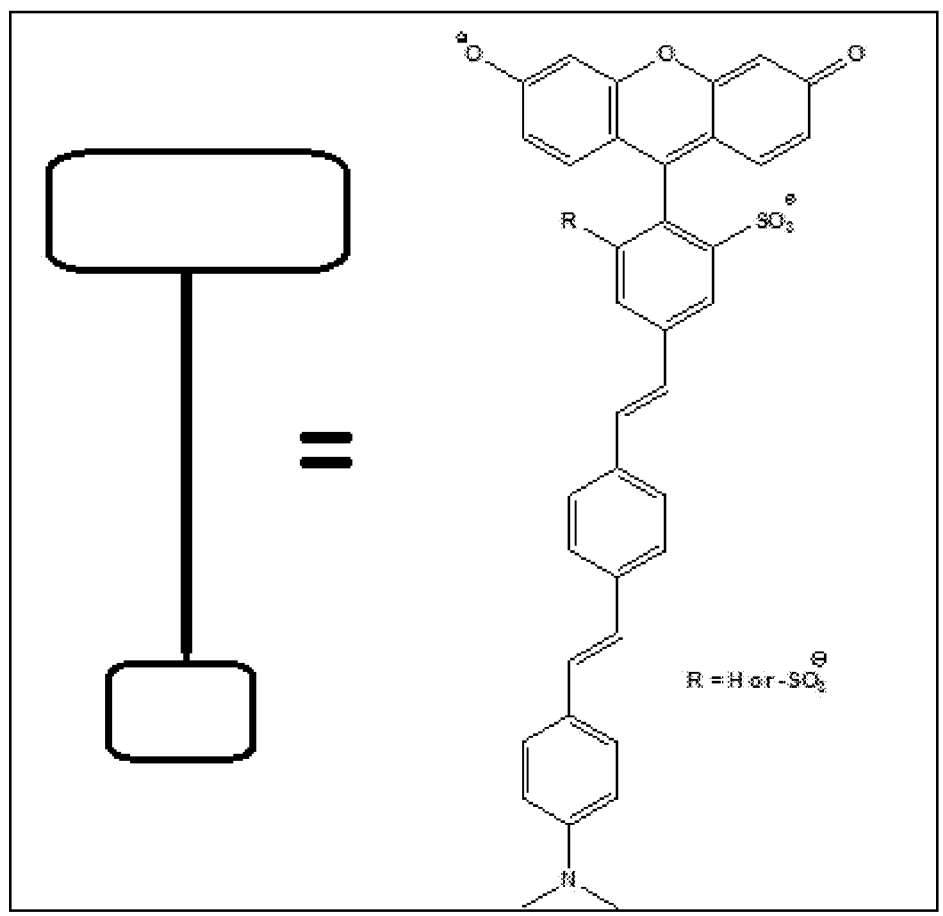
FIG. 3A-F shows orientation of ms and ds VF dyes. Schematic representation of (A) VF dye alignment in the plasma membrane. (B) Maximum voltage sensitivity is predicted when theta=0° (left) and is lowest when theta=90°. (C) Intermediate values of theta (right) reduce voltage sensitivity. Snapshots of MD simulations in POPC lipid bilayers show (D) msVF and (E) dsVF. Yellow arrows indicate principal components. (F) Plot of probability density vs. angle of displacement between the $3^{rd}$ principle component (the long axis) of VF dyes and the membrane normal.
Figure 3B:
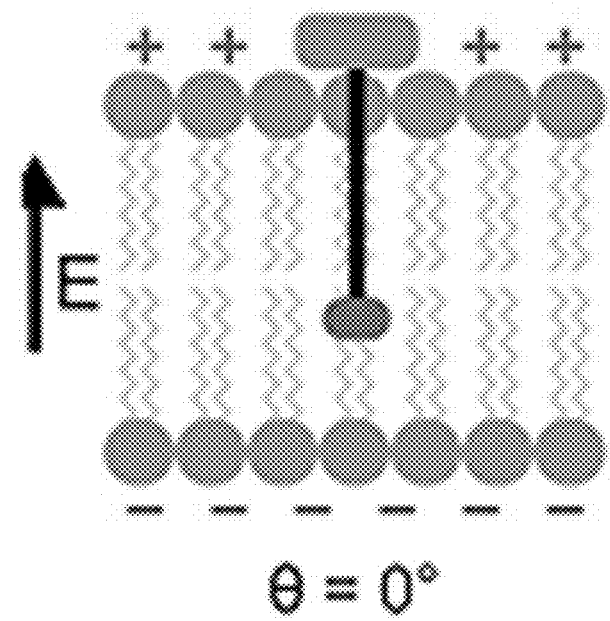
Figure 3C:
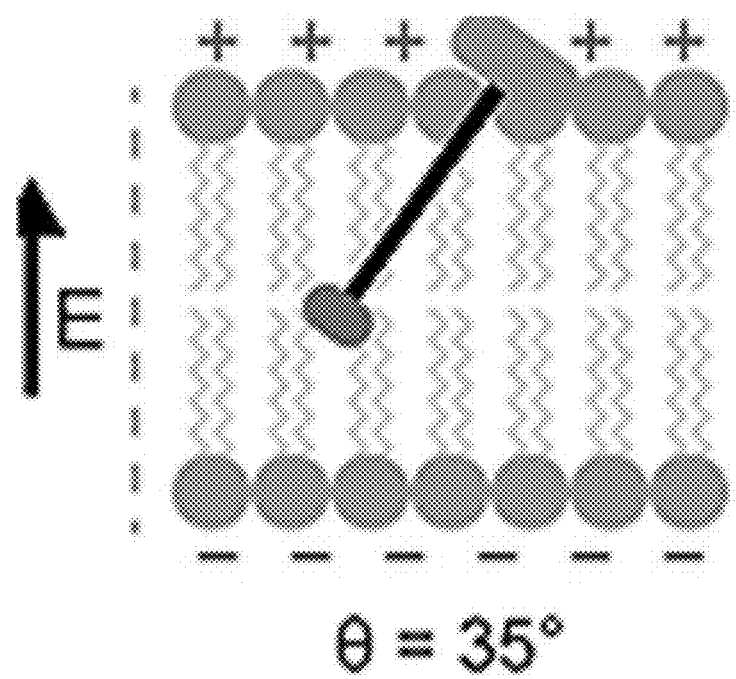

By extension to PeT-based voltage sensitive dyes, the voltage sensitivity should be proportional to the change in driving force for PeT, which can be modeled by the same equation. Because the interaction between the electron transferred and the membrane potential is highest when the electron transfer vector and electric field vectors are aligned and at a minimum when perpendicular, equation (1) can be rewritten as equation 2:

$$\Delta G = qrE \cos \theta \quad \text{(Eq. 2)}$$

where $\theta$ is the angle of displacement, or tilt, between the electron transfer vector and the electric field vector (See FIG. 3B-C). The initial assumption was that the tile angle $\theta$ was close to 0°, thus giving the maximum voltage sensitivity for a given dye, where q, r, and E remain constant. To test this hypothesis and ascertain how the compounds disclosed herein orient in the membrane, molecular modeling was turned to in order to measure the tilt angle of VF2.1.Cl in a simulated lipid bilayer. VF2.1.Cl was parameterized via a quantum mechanical approach and then ps molecular dynamics (MD) simulations in a POPC lipid bilayer were then performed, as a simplified model for a mammalian cell. By modeling the behavior of the VF2.1.Cl in a POPC lipid bilayer, observations regarding the tilt angle and possible structural modifications could be evaluated. Based upon which, compounds of the disclosure could be synthesized and changes in voltage sensitivity could be assessed. 200 ns molecular dynamics simulations of VF2.1.Cl can be performed in a pure POPC membrane and sampled the tilt angle $\theta$ every 5 ps via principle component analysis. VF2.1.Cl demonstrated considerable tilt in both the plane parallel to the molecular wire and perpendicular to it, resulting in an average tilt angle of 34° (see FIG. 3D-E). Furthermore, the molecule appeared to be rather "floppy" in the membrane, with a standard deviation of the tilt angle of 14° and a cycling period of approximately 30 ns. An average tilt angle of 34° implies that the voltage sensitivity of VF2.1.Cl is only about 83% (cosine of 34°) of the theoretical maximum, assuming q and r remain the same. It was hypothecated that compounds exhibiting a straightened rigid structure in the membrane would allow for a voltage sensitivity enhancement of up to 20%.

It was reasoned that the tilt angle of a compound disclosed herein could be reduced in a straightforward manner by adding a second sulfonate group in the ortho-position on the meso-aryl ring of the xanthene chromophore. It was hoped that the compounds of the disclosure by comprising two opposing sulfonate groups at the 2- and 6-positions, would have both reduced overall tilt angle and increased rigidity, resulting in smaller fluctuations in tilt angle relative to VF dyes comprising only one sulfo-group.

Also provided herein is a molecular modeling approach to study the effects of orientation on the voltage sensitivity of the compounds of the disclosure as well as other VF dyes. Further, the molecular modeling can be used to produce compounds with greater voltage sensitivity than previous generations of VF dyes. In certain embodiment, the disclosure provides for the design and synthesis of compounds comprising disulfonated fluoresceins, a novel group of xanthene molecules with increased water solubility. In further embodiments, the compounds disclosed herein comprise a diethylmethoxy molecular wire group. The diethylmethoxy molecular wire group not only exhibits similar electron donating properties as previously reported wires, but utilizes a more convenient synthesis.

The disclosure provides for compounds that comprise disulfonated fluoresceins. The compounds of the disclosure are more rigid then previously disclosed VF dyes. One of the compounds of the disclosure, disulfoVF2.2(OMe).Cl shows the highest voltage sensitivity observed in PeT-based voltage sensors thus far (63% $\Delta$F/F per 100 mV). Additionally, it was demonstrated herein that disulfoVF2.2(OMe).Cl can be used to detect membrane potential changes in rat hippocampal neurons.

The improved voltage sensitivity of the compounds disclosed herein (e.g., disulfoVF2.2(OMe).Cl) facilitates voltage imaging in systems that naturally reduce signal-to-noise, such as low-power illumination, thicker tissue samples, and long-term imaging. Moreover, the methods disclosed herein allow for further development of compounds that exhibit higher voltage sensitivity than first generation VF dyes. For example, the disclosure further provides in certain embodiments for compounds which comprise rhodamines or silicon-rhodamines groups, as opposed to xanthene groups.

Described herein are the design, synthesis, and characterization of compounds for use in voltage sensing applications. The compounds of the disclosure display bright, membrane-localized fluorescence, are highly photostable, and extremely voltage-sensitive. The compounds can detect action potentials in cultured hippocampal neurons and interface readily with a number of other optical tools. According, the compounds of the disclosure are ideally suited for multicolor imaging with GFP, $Ca^{2+}$ indicators like GCaMP, voltage sensors based on cpGFP such as ASAP1, as well as optogenetic tools like ChR2. Use of the compounds of the disclosure alongside ChR2 permits non-invasive recording and control of membrane potential in single cells and in neuronal microcircuits.

Molecular probes comprising the compounds of the disclosure fill an important role in measuring membrane potential. The compounds of the disclosure do not require any genetic manipulation, can be delivered to all cell types, respond rapidly to fast voltage changes, and can be tuned across a wide color range. Further, in certain embodiments disclosed herein, the compounds disclosed herein comprise a phenylenevinylene molecular wire based platform. The emission profile of the compounds disclosed herein can therefore be tuned based upon structural modification of the molecular wire platform or by making minor changes to the fluorophore. Accordingly, the compounds of the disclosure are invaluable tools for mapping membrane potential dynamics in a variety of systems. The compounds of the disclosure can be used with fluorescent stains for organelles, $Ca^{2+}$ indicators, and voltage-sensitive fluorescent proteins; and in conjunction with optogenetic actuators like Channel-Rhodopsin2 (ChR2) (which utilizes blue light), the spectral profile of the compounds of the disclosure enable optical electrophysiology in neurons. The high speed, sensitivity, photostability and fluorescence profiles of compounds of the disclosure make the compounds a useful platform for studying neuronal activity non-invasively.

In one embodiment, the disclosure provides for a compound having the structure of Formula I:

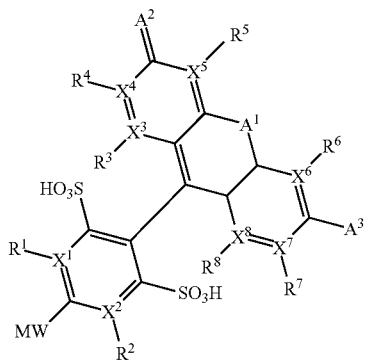

Formula I wherein, $A^1$ is selected from $CH_2$, CHR', $CR'_2$, NH, O, S, Se, Te, $SiH_2$, SiHR', $SiR'_2$, $GeH_2$, GeHR', $GeR'_2$, $SnH_2$, SnHR', $SnR'_2$, $PbH_2$, PbHR', or $PbHR'_2$, wherein R' is selected from the group consisting of D, optionally substituted FG, optionally substituted ($C_1$-$C_{12}$)alkyl, optionally substituted ($C_2$-$C_{10}$)heteroalkyl, optionally substituted ($C_1$-$C_{12}$) alkenyl, optionally substituted ($C_2$-$C_{10}$)heteroalkenyl, optionally substituted ($C_1$-$C_{12}$)alkynyl, and optionally substituted ($C_2$-$C_{10}$)heteroalkynyl;

$A^2$ is selected from $NH_2$, S and O;

$A^3$ is selected from $NH_2$, OH, SH and methoxy;

$X^1$-$X^8$ are independently selected from N or C, wherein when an X group is an N, then the R group is absent; and $R^1$-$R^8$ are independently selected from H, D, optionally substituted FG, optionally substituted ($C_1$-$C_{12}$)alkyl, optionally substituted ($C_2$-$C_{10}$)heteroalkyl, optionally substituted ($C_1$-$C_{12}$)alkenyl, optionally substituted ($C_2$-$C_{10}$)heteroalkenyl, optionally substituted ($C_1$-$C_{12}$) alkynyl, optionally substituted ($C_2$-$C_{10}$)heteroalkynyl, optionally substituted ($C_3$-$C_{12}$)cycloalkyl, optionally substituted ($C_5$-$C_{12}$)cycloalkenyl, optionally substituted aryl, optionally substituted heterocycle, optionally substituted mixed ring system, wherein one or more adjacent R groups can be linked together to form one or more substituted rings selected from the group comprising ($C_3$-$C_{12}$)cycloalkyl, ($C_3$-$C_{12}$)cycloalkenyl, heterocycle, aryl, and mixed ring system; and MW is a molecular wire group.

In another embodiment, the disclosure provides for a compound comprising the structure of Formula II:

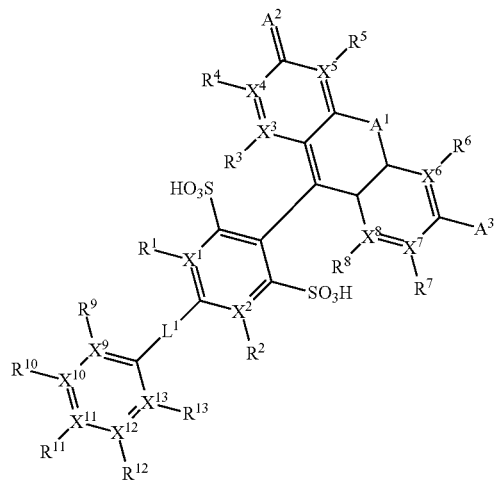

Formula II wherein, $L^1$ is selected from the group consisting of:

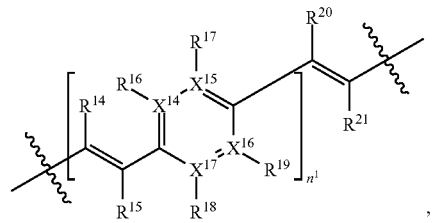

,

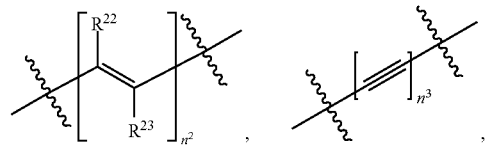

,

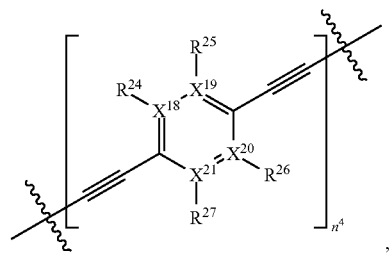

,

-continued

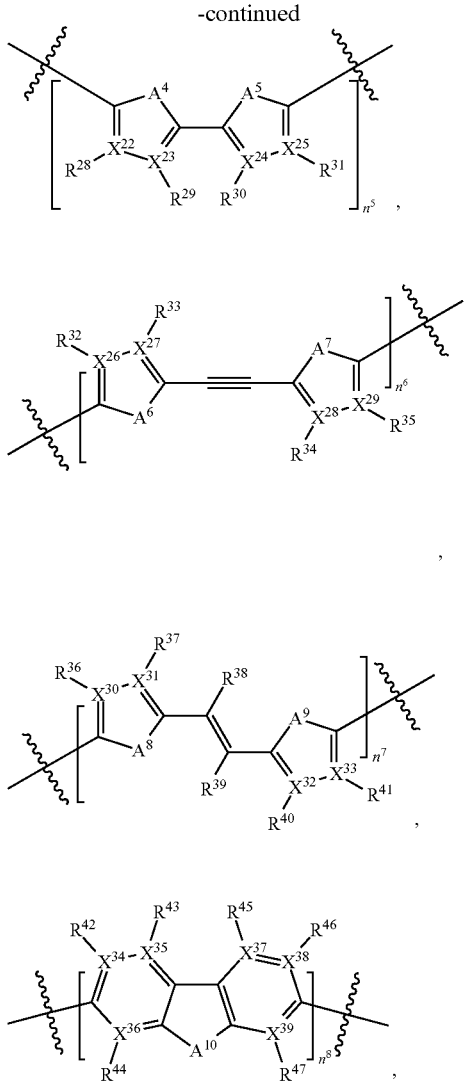

and any combination of the foregoing;

$A^1$, $A^4$-$A^{10}$ are each independently selected from $CH_2$, $CHR'$, $CR'_2$, $NH$, $O$, $S$, $Se$, $Te$, $SiH_2$, $SiHR'$, $SiR'_2$, $GeH_2$, $GeHR'$, $GeR'_2$, $SnH_2$, $SnHR'$, $SnR'_2$, $PbH_2$, $PbHR'$, or $PbHR'_2$, wherein R' is selected from the group consisting of D, optionally substituted FG, optionally substituted ($C_1$-$C_{12}$) alkyl, optionally substituted ($C_1$-$C_{11}$)heteroalkyl, optionally substituted ($C_1$-$C_{12}$)alkenyl, optionally substituted ($C_1$-$C_{11}$) heteroalkenyl, optionally substituted ($C_1$-$C_{12}$)alkynyl, and optionally substituted ($C_1$-$C_{11}$)heteroalkynyl;

$A^2$ is selected from $NH_2$, S or O;

$A^3$ is selected from $NH_2$, OH, SH and methoxy;

$X^1$-$X^{39}$ are independently selected from N or C, wherein when an X group is an N, then the R group is absent; and $R^1$-$R^{47}$ are independently selected from H, D, optionally substituted FG, optionally substituted ($C_1$-$C_{12}$)alkyl, optionally substituted ($C_2$-$C_{10}$)heteroalkyl, optionally substituted ($C_1$-$C_{12}$)alkenyl, optionally substituted ($C_2$-$C_{10}$)heteroalkenyl, optionally substituted ($C_1$-$C_{12}$) alkynyl, optionally substituted ($C_2$-$C_{10}$)heteroalkynyl, optionally substituted ($C_3$-$C_{12}$)cycloalkyl, optionally substituted ($C_5$-$C_{12}$)cycloalkenyl, optionally substituted aryl, optionally substituted heterocycle, optionally substituted mixed ring system, wherein one or more adjacent R groups can be linked together to form one or more substituted rings selected from the group comprising ($C_3$-$C_{12}$)cycloalkyl, ($C_3$-$C_{12}$)cycloalkenyl, heterocycle, aryl, and mixed ring system; and $n^1$-$n^8$ are independently an integer selected from 0 to 10.

In another embodiment, the disclosure provides for a compound comprising the structure of Formula III:

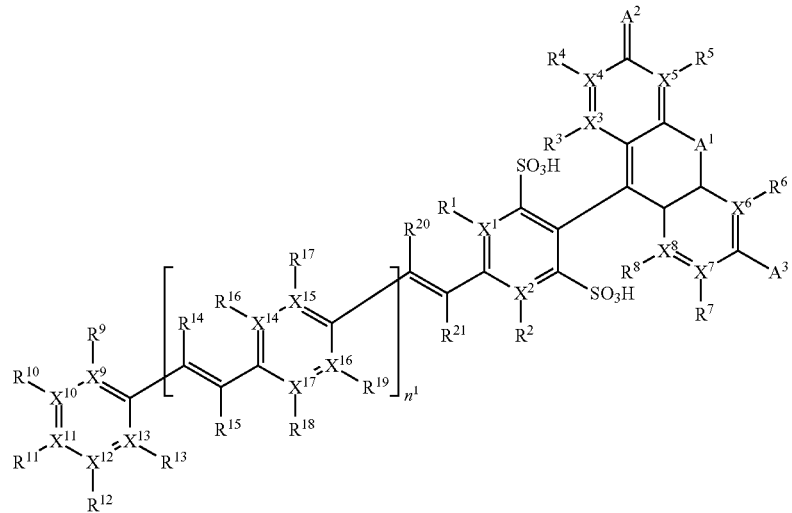

Formula III wherein, $A^1$ is selected from $CH_2$, CHR', $CR'_2$, NH, O, S, Se, Te, $SiH_2$, SiHR', $SiR'_2$, $GeH_2$, GeHR', $GeR'_2$, $SnH_2$, SnHR', $SnR'_2$, $PbH_2$, PbHR', or $PbHR'_2$, wherein R' is selected from the group consisting of D, optionally substituted FG, optionally substituted ($C_1$-$C_{12}$)alkyl, optionally substituted ($C_2$-$C_{10}$)heteroalkyl, optionally substituted ($C_1$-$C_{12}$)alkenyl, optionally substituted ($C_2$-$C_{10}$)heteroalkenyl, optionally substituted ($C_1$-$C_{12}$)alkynyl, and optionally substituted ($C_2$-$C_{10}$)heteroalkynyl;

$A^2$ is $NH_2$ or O;

$A^3$ is selected from $NH_2$, OH and methoxy;

$X^1$-$X^{17}$ are independently selected from N or C, wherein when an X group is an N, then the R group is absent; and $R^1$-$R^{21}$ are independently selected from H, D, optionally substituted FG, optionally substituted ($C_1$-$C_{12}$)alkyl, optionally substituted ($C_2$-$C_{10}$)heteroalkyl, optionally substituted ($C_1$-$C_{12}$)alkenyl, optionally substituted ($C_2$-$C_{10}$)heteroalkenyl, optionally substituted ($C_1$-$C_{12}$) alkynyl, optionally substituted ($C_2$-$C_{10}$)heteroalkynyl, optionally substituted ($C_3$-$C_{12}$)cycloalkyl, optionally substituted ($C_5$-$C_{12}$)cycloalkenyl, optionally substituted aryl, optionally substituted heterocycle, optionally substituted mixed ring system, wherein one or more adjacent R groups can be linked together to form one or more substituted rings selected from the group comprising ($C_3$-$C_{12}$)cycloalkyl, ($C_3$-$C_{12}$)cycloalkenyl, heterocycle, aryl, and mixed ring system; and $n^1$ is an integer selected from 0 to 10.

In another embodiment, the disclosure provides for a compound having the structure of Formula III(a):

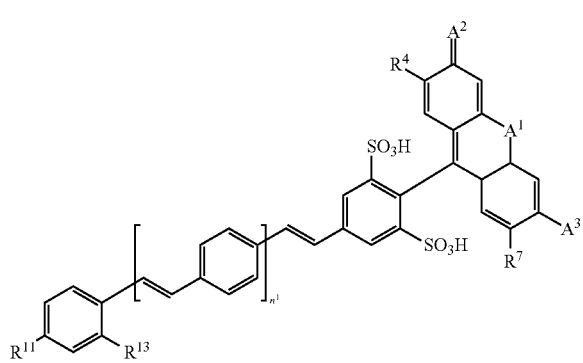

Formula III(a)

wherein, $A^1$ is selected from $CH_2$, CHR', $CR'_2$, NH, O, S, Se, Te, $SiH_2$, SiHR', $SiR'_2$, $GeH_2$, GeHR', $GeR'_2$, $SnH_2$, SnHR', $SnR'_2$, $PbH_2$, PbHR', or $PbHR'_2$, wherein R' is selected from the group consisting of D, optionally substituted FG, optionally substituted ($C_1$-$C_6$)alkyl, optionally substituted ($C_2$-$C_6$)heteroalkyl, optionally substituted ($C_1$-$C_6$)alkenyl, optionally substituted ($C_2$-$C_5$)heteroalkenyl, optionally substituted ($C_1$-$C_6$)alkynyl, and optionally substituted ($C_2$-$C_5$)heteroalkynyl;

$A^2$ is $NH_2$ or O;

$A^3$ is $NH_2$ or OH;

$R^4$ and $R^7$ are independently selected from H, F, and Cl;

$R^{11}$ is selected from $NH_2$, $NH(R^{50})$, $N(R^{50})_2$, wherein $R^{50}$ is a ($C_1$-$C_3$) alkyl;

$R^{13}$ is selected from H, CN, alkoxy, OH, halo and amino; and $n^1$ is an integer selected from 0 to 5.

In yet another embodiment, the disclosure provides for a compound having the structure of Formula III(b):

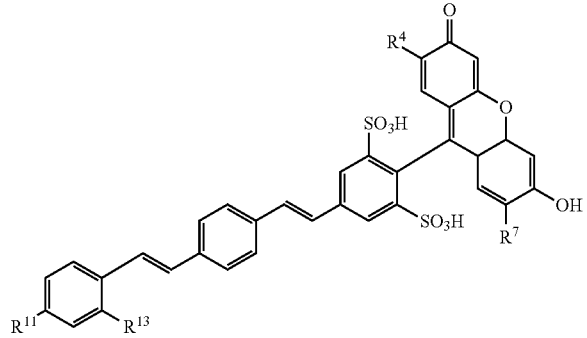

Formula III(b)

wherein, $R^4$ and $R^7$ are independently selected from H, F, and Cl;

$R^{11}$ is selected from $NH_2$, $NH(R^{50})$, $N(R^{50})_2$, wherein $R^{50}$ is a ($C_1$-$C_3$) alkyl; and $R_{13}$ is H or a methoxy.

It should be further noted, that for any structure depicted herein (e.g., Formula I, II, III, III(a), III(b)) that any resonance form of the foregoing structures is further contemplated herein.

It should be further understood, that while the formulae depicted herein are indicated as being an uncharged species, the charged species are also contemplated herein. Accordingly, the formulae should be viewed as providing for charged groups (e.g., $SO_3^-$) in addition to the depicted uncharged groups (e.g., $SO_3H$).

In a certain embodiments described herein, the compounds of the disclosure are characterized by being voltage sensitive and emit light upon excitation with incident light. Advantages of the compounds described herein include being more rigid than standard VF dyes, and having higher voltage sensitivities.

In a particular embodiment, the disclosure provides for a sensor comprising a compound disclosed herein for interrogating membrane potential dynamics in neurons. In yet a further embodiment, the sensor is triggered by photoinduced electron transfer (PeT).

In a certain embodiment, the disclosure provides methods for using the compounds disclosed herein, comprising exciting the compound with incident light; measuring the emission of light by the compound. In a further embodiment, the light emitted by the compound is quantitated. In particular embodiments, the compounds disclosed herein can be used in methods for cell imaging, drug screening and voltage sensing. In a further embodiment, the compounds are ideally suited for interrogating membrane potential dynamics in neurons.

In yet a further embodiment, the compounds disclosed herein are useful for screening drugs that affect membrane potential/ion channels or for screening drug safety and/or efficacy. In a further embodiment, the method further comprises: contacting the cells with one or more additional optogenetic tools; and imaging the cells be detecting light emissions at one or more additional wavelengths. Examples of optogenetic tools include, but are not limited to, GFP, $Ca^{2+}$ indicators, voltage sensors based on cpGFP, and ChannelRhodopsin2 (ChR2).

In a particular embodiment, the disclosure further provides a method to measure changes in membrane potential in an excitable cell comprising: contacting the excitable cell with a compound disclosed herein; stimulating the cell to evoke action potentials; and measuring action potential firing by optical or electrical sampling. In another embodiment, the optical sampling is measured using an electron multiplying charge couple device. In yet another embodiment, the excitable cell is stimulated using a whole-cell current clamp or by field stimulation. Examples of excitable cells include, but are not limited to, neurons, cardiomyocytes, myocytes, or secretory cells. In yet another embodiment, the method interrogates membrane potentials of a neuron.

Kits are also a feature of this disclosure. Embodiments of the kits include at least one compound according to any one of general formulas described herein. Such kits are suitable for voltage sensing applications based upon photoinduced electron transfer. In other embodiments, such kits are suitable for drug screening (e.g., screening drugs that affect membrane potential/ion channels or screening for drug safety and efficacy). In some embodiments, the kits also include at least one buffer solution in which the compound, when used in conjunction with excitable cells, will allow for sensing changes in the membrane potential of the excitable cell. Alternatively, the buffer may be provided as a concentrated solution, which is subsequently diluted prior to use. In certain embodiments, the compound may be premeasured into one or more containers (e.g., test tubes or cuvettes), and the detection is subsequently performed by adding the buffer and test sample to the container.

The kits also may include one or more containers, such as a disposable test tube or cuvette, in which the detection can be performed. The kits may further include instructions for performing the detection.

EXAMPLES

General Method for Chemical Synthesis and Characterization

Chemical reagents and anhydrous solvents were purchased from commercial suppliers and used without further purification. All reactions were carried out in oven-dried flasks under an inert atmosphere of $N_2$. Thin layer chromatography (TLC) (Silicycle, F254, 250 μm) was performed on glass backed plates pre-coated with silica gel and were visualized by fluorescence quenching under UV light. Flash column chromatography was performed on Silicycle Silica Flash F60 (230-400 Mesh) using a forced flow of air at 0.5-1.0 bar. NMR spectra were measured on a Bruker AV-600 MHz, 150 MHz. Chemical shifts are expressed in parts per million (ppm) and are referenced to $d_6$-DMSO, 2.50 ppm. Coupling constants are reported as Hertz (Hz). Splitting patterns are indicated as follows: s, singlet; d, doublet; sep, septet dd, doublet of doublet; ddd, doublet of double of doublet; dt, doublet of triplet; td, triplet of doublet; m, multiplet. High-resolution mass spectra (ESI EI) were measured by the QB3/Chemistry mass spectrometry service at University of California, Berkeley. High performance liquid chromatography (HPLC) and low resolution ESI Mass Spectrometry were performed on an Agilent Infinity 1200 analytical instrument coupled to an Advion CMS-L ESI mass spectrometer. Columns used for the analytical and semi-preparative HPLC were Phenomenex Luna C18(2) (4.6 mm I.D.×150 mm) and Phenomenex Luna 5 μm C18(2) (10 mm I.D.×150 mm) columns with a flow rate of 1.0 and 3.0 mL/min, respectively. The mobile phase were MQ-H2O with 0.05% formic acid (eluent A) and HPLC grade acetonitrile with 0.05% formic acid (eluent B). Signals were monitored at 254 and 460 nm in 20 min with gradient 5-100% eluent B.

Spectroscopic Studies.

Stock solutions of VF dyes were prepared in DMSO (1.0-10 mM) and diluted with PBS (100 mM $Na_2HPO_4$, pH 7.4, 0.1% Triton-X). UV-Vis absorbance and fluorescence spectra were recorded using a Shimadzu 2501 Spectrophotometer (Shimadzu) and a Quantamaster Master 4 L-format scanning spectrofluorometer (Photon Technologies International). The fluorometer is equipped with an LPS-220B 75-W xenon lamp and power supply, A-1010B lamp housing with integrated igniter, switchable 814 photon-counting/analog photomultiplier detection unit, and MD5020 motor driver. Samples were measured in 1-cm path length quartz cuvettes (Starna Cells).

Preparation of Formylbenzenesulfonic Acids

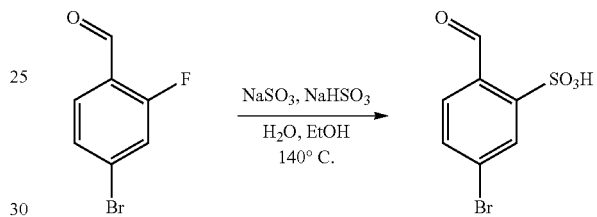

Synthesis of 5-bromo-2-formylbenzenesulfonic acid 4-bromo-2-fluorobenzaldehyde (3.0 g, 14.78 mmol) was placed in a long-necked bomb flask and dissolved in a 1:1 mixture of ethanol and water. Sodium sulfite (1.49 g, 11.82 mmol) and sodium bisulfite (123 mg, 1.18 mmol) were added and the reaction was stirred for 16 hours at 140 degrees Celsius. The reaction mixture, after cooling, was poured into methanol while stirring so as to make 20% aqueous content of the whole volume. This process precipitated the inorganic salts, which were then removed by vacuum filtration. The solvent from the filtrate was removed under reduced pressure to obtain a solid residue, which was triturated with methanol/ethyl ether to produce a fluffy white solid (2.82 g, 72%). $^1$H NMR (400 MHz, DMSO-$d_6$) δ 10.85 (s, 1H), 8.09 (d, J=1.7 Hz, 1H), 7.72 (d, J=7.9 Hz, 1H), 7.66 (dd, J=7.4, 1.5 Hz, 1H). $^{13}$C NMR (226 MHz, DMSO) δ 192.65, 151.31, 132.34, 131.46, 129.58, 128.88, 126.97. HR-ESI-MS m/z for $C_7H_4BrO_4S^-$ calcd: 262.9092 found: 262.9017.

Synthesis of
5-bromo-2-formylbenzene-1,3-disulfonic acid

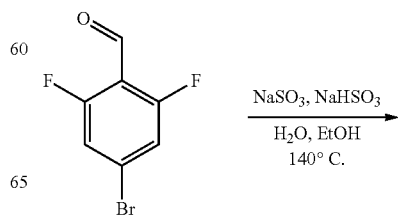

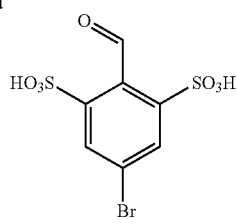

4-bromo-2,6-difluorobenzaldehyde (1.0 g, 4.52 mmol) was placed in a long-necked bomb flask and dissolved in 10 mL of a 1:1 mixture of ethanol and water. Sodium sulfite (1.14 g, 9.05 mmol) and sodium bisulfite (94 mg, 0.90 mmol) were added and the reaction was stirred for 16 hours at 140 degrees Celsius. The reaction mixture, after cooling, was poured into methanol while stirring so as to make 20% aqueous content of the whole volume. This process precipitated the inorganic salts, which were then removed by vacuum filtration. The solvent from the filtrate was removed under reduced pressure to obtain a solid residue, which was triturated with methanol/ethyl ether to produce a fluffy white solid (1.19 g, 76%), which was judged to be pure by NMR. 1H NMR (400 MHz, Methanol-d4) δ 10.62 (s, 1H), 8.12 (s, 2H). $^{13}$C NMR (226 MHz, DMSO) δ 186.45, 165.53, 155.33, 130.84. HR-ESI-MS m/z for $C_7H_4BrO_7S_2^-$ calcd: 342.8660 found: 342.8596.

Synthesis of 5-bromosulfofluorescein

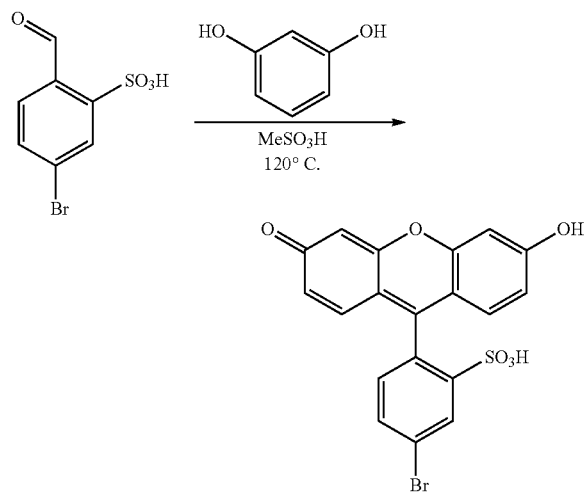

5-bromo-2-formylbenzenesulfonic acid (300 mg, 1.13 mmol) and resorcinol (249 mg, 2.26 mmol) were placed in a roundbottom flask dissolved in 3 mL of neat methanesulfonic acid and stirred for 16 hours at 120 degrees Celsius. After cooling, the reaction mixture was poured into 5 mL water, resulting in precipitation of a brown solid. The solid was isolated via vacuum filtration (400 mg, 79%) and judged to be pure by NMR. $^1$H NMR (300 MHz, DMSO-d$_6$) δ 8.07 (s, 1H), 7.83 (d, J=6.8 Hz, 1H), 7.44 (d, J=9.2 Hz, 2H), 7.33 (s, 2H), 7.27 (d, J=8.3 Hz, 1H), 7.18 (d, J=8.4 Hz, 2H). $^{13}$C NMR (226 MHz, DMSO) δ 170.84, 167.13, 158.57, 158.47, 148.63, 134.74, 131.77, 130.21, 119.48, 117.07, 106.24, 102.51, 101.72. HR-ESI-MS m/z for $C_{19}H_{10}BrO_6S^-$ calcd: 444.9460 found: 444.9379.

Synthesis of 5-bromo-2',7'-dichlorosulfofluorescein

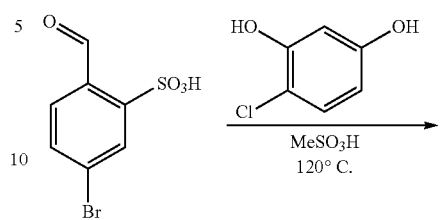

5-bromo-2-formylbenzenesulfonic acid (250 mg, 0.94 mmol) and 4-chlororesorcinol (272 mg, 1.89 mmol) were placed in a roundbottom flask dissolved in 3 mL of neat methanesulfonic acid and stirred for 16 hours at 120 degrees Celsius. After cooling, the reaction mixture was poured into 5 mL water, resulting in precipitation of a reddish-brown solid. The solid was isolated via vacuum filtration (380 mg, 78%) and judged to be pure by NMR. 1H NMR (400 MHz, DMSO-d6) δ 8.06 (s, 1H), 7.75 (d, J=8.0 Hz, 1H), 7.22 (d, J=8.1 Hz, 1H), 6.89 (s, 2H), 6.73 (s, 2H). $^{13}$C NMR (226 MHz, DMSO) δ 157.13, 153.54, 131.98, 131.89, 130.20, 129.81, 129.62, 122.76, 115.78, 109.47, 107.39, 103.68, 103.32. HR-ESI-MS m/z for $C_{19}H_8BrCl_2O_6S^-$ calcd: 512.8680 found: 512.8598.

Synthesis of 5-bromo-2', 7'-difluorosulfofluorescein

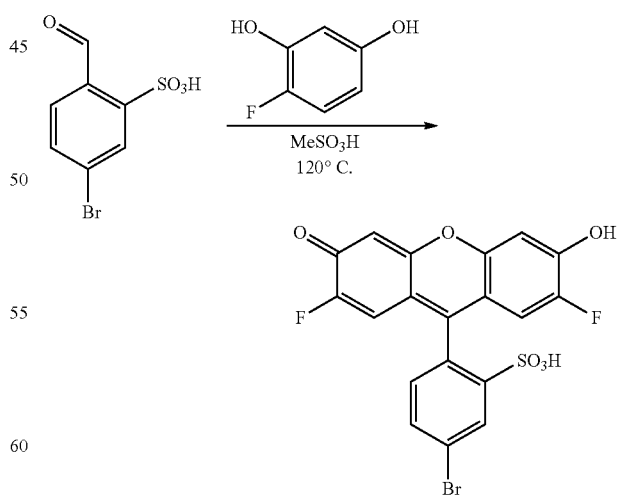

5-bromo-2-formylbenzenesulfonic acid (300 mg, 1.13 mmol) and 4-fluororesorcinol (290 mg, 2.26 mmol) were placed in a roundbottom flask dissolved in 3 mL of neat methanesulfonic acid and stirred for 16 hours at 120 degrees Celsius. After cooling, the reaction mixture was poured into 5 mL water, resulting in precipitation of a brown-black solid. The solid was isolated via vacuum filtration (463 mg, 85%) and judged to be pure by NMR. $^1$H NMR (400 MHz, DMSO-d$_6$) δ 8.05 (d, J=2.0 Hz, 1H), 7.73 (d, J=6.9 Hz, 1H), 7.45 (d, J=8.2 Hz, 1H), 6.78 (d, J=7.1 Hz, 2H), 6.58 (d, J=11.4 Hz, 2H). $^{13}$C NMR (226 MHz, DMSO) δ 153.57, 151.96, 150.85, 148.58, 132.07, 131.76, 130.29, 128.27, 122.86, 115.24, 113.54, 113.45, 104.26. HR-ESI-MS m/z for C$_{19}$H$_8$BrF$_2$O$_6$S$^-$ calcd: 480.9271 found: 480.9187.

Synthesis of 5-bromodisulfofluorescein

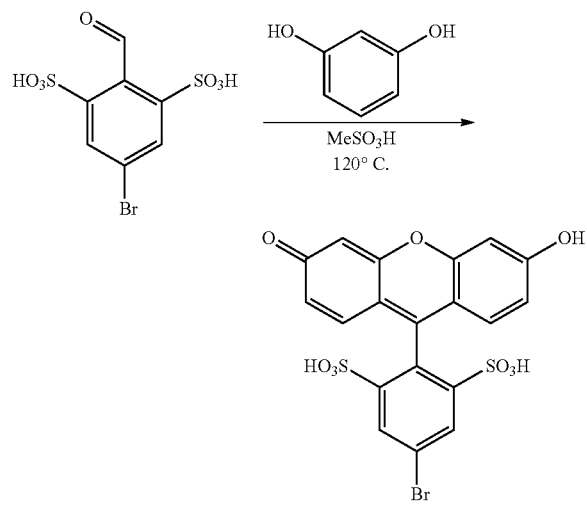

5-bromo-2-formylbenzene-2,6-disulfonic acid (300 mg, 0.87 mmol) and resorcinol (191 mg, 1.74 mmol) were placed in a roundbottom flask dissolved in 3 mL of neat methanesulfonic acid and stirred for 16 hours at 120 degrees Celsius. After cooling, the reaction mixture was diluted with 3 mL dichloromethane and poured into 50 mL diethyl ether, resulting in precipitation of a brown solid. The solid was isolated via vacuum filtration (129 mg, 28%) and judged to be pure by NMR. 1H NMR (600 MHz, DMSO-d6) δ 8.11 (s, 2H), 7.36 (d, J=9.2 Hz, 2H), 7.26 (s, 2H), 7.08 (d, J=6.4 Hz, 2H). $^{13}$C NMR (226 MHz, DMSO) δ 170.00, 157.81, 149.34, 149.32, 135.70, 133.36, 130.65, 123.69, 118.56, 118.17, 100.93. HR-ESI-MS m/z for C$_{19}$H$_{10}$BrO$_9$S$_2$$^-$ calcd: 524.9028 found: 524.8944.

Synthesis of 5-bromo-2',7'-dichlorodisulfofluorescein

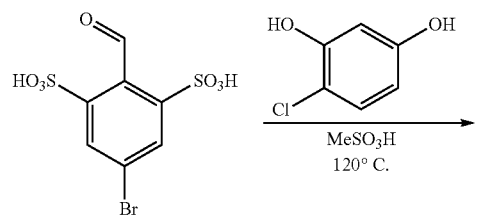

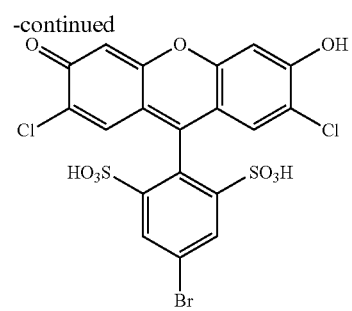

5-bromo-2-formylbenzene-2,6-disulfonic acid (250 mg, 0.72 mmol) and 4-chlororesorcinol (209 mg, 1.45 mmol) were placed in a roundbottom flask dissolved in 3 mL of neat methanesulfonic acid and stirred for 16 hours at 120 degrees Celsius. After cooling, the reaction mixture was diluted with 3 mL dichloromethane and poured into 50 mL diethyl ether, resulting in precipitation of a reddish-brown solid. The solid was isolated via vacuum filtration (200 mg, 46%) and judged to be pure by NMR. 1H NMR (600 MHz, DMSO-d6) δ 8.11 (s, 2H), 6.82 (s, 2H), 6.67 (s, 2H). $^{13}$C NMR (226 MHz, DMSO) δ 155.04, 149.45, 131.49, 130.81, 124.17, 123.49, 122.48, 117.72, 102.47. HR-ESI-MS m/z for C$_{19}$H$_8$BrCl$_2$O$_9$S$_2$$^-$ calcd: 592.8248 found: 522.8157.

Synthesis of 5-bromo-2',7'-difluorodisulfofluorescein

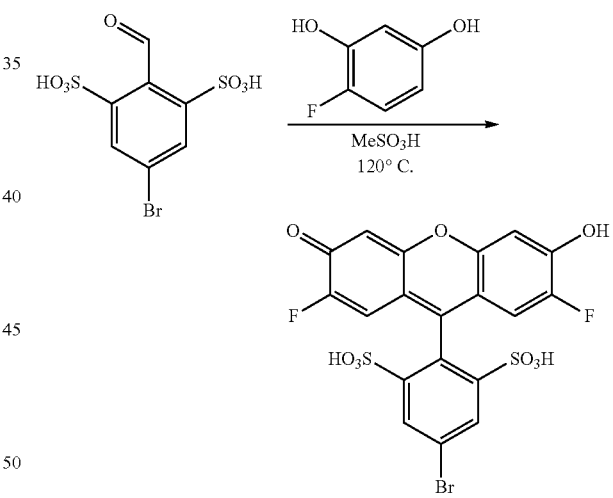

5-bromo-2-formylbenzene-2,6-disulfonic acid (300 mg, 0.87 mmol) and 4-fluororesorcinol (222 mg, 1.74 mmol) were placed in a roundbottom flask dissolved in 3 mL of neat methanesulfonic acid and stirred for 16 hours at 120 degrees Celsius. After cooling, the reaction mixture was diluted with 3 mL dichloromethane and poured into 50 mL diethyl ether, resulting in precipitation of a reddish-brown solid. The solid was isolated via vacuum filtration (330 mg, 67%) and judged to be pure by NMR. $^1$H NMR (300 MHz, DMSO-d$_6$) δ 8.11 (s, 2H), 7.16 (d, J=6.7 Hz, 2H), 6.84 (d, J=11.1 Hz, 2H). $^{13}$C NMR (226 MHz, DMSO) δ 161.45, 161.37, 154.30, 151.48, 150.37, 149.45, 131.27, 124.34, 123.26, 118.05, 118.01, 116.10, 116.01, 103.66. HR-ESI-MS m/z for C$_{19}$H$_8$BrF$_2$O$_9$S$_2$$^-$ calcd: 560.8839 found: 560.8752.

Synthesis of monosulfoVF2.2(OMe).H

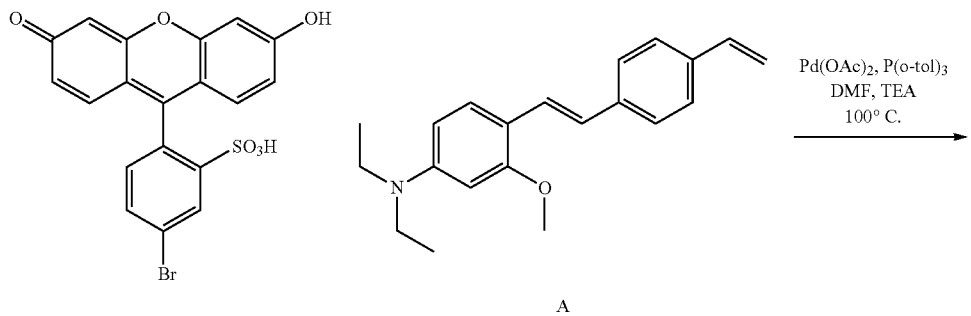

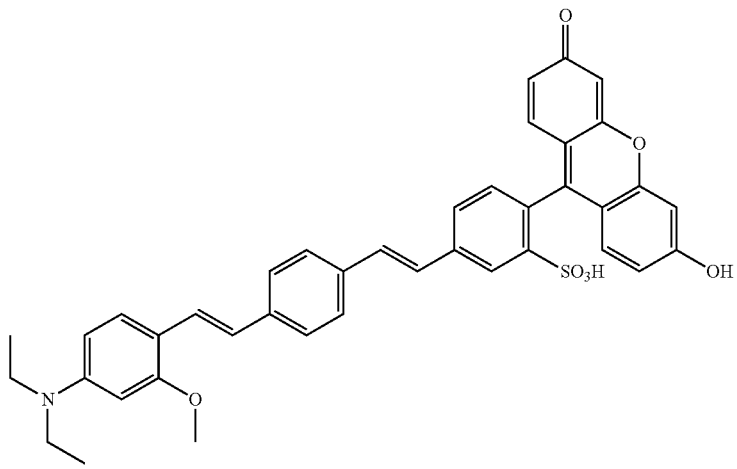

5-bromosulfofluorescein (100 mg, 0.22 mmol), A (83 mg, 0.27 mmol), palladium acetate (1 mg, 0.045 mmol), and P(o-tol)$_3$ (2.7 mg, 0.09 mmol) were placed in an oven-dried Schlenk flask. The flask was sealed and evacuated/backfilled with nitrogen (3×). Anhydrous DMF (1 mL) and anhydrous Et$_3$N (1 mL) were added via syringe and the reaction was stirred for 16 hours at 100 degrees Celsius. After cooling, the reaction mixture was diluted with 3 mL dichloromethane and filtered through celite, which was then washed with methanol. The solvent was removed from the filtrate via rotary evaporation and the resulting residue was dissolved in 5 mL dichloromethane. The mixture was then poured into diethyl ether, resulting in precipitation of a brown solid. The solid was isolated via vacuum filtration (66 mg, 44%). A small amount of material was purified via RP-HPLC for further characterization. $^1$H NMR (900 MHz, DMSO-d$_6$) δ 8.15 (s, 2H), 7.94 (s, 2H), 7.75 (d, J=8.2 Hz, 2H), 7.64 (d, J=8.0 Hz, 2H), 7.50 (d, J=7.9 Hz, 4H), 7.38 (d, 14.1 Hz, 2H), 7.34 (d, J=16.5 Hz, 2H), 7.21-7.17 (m, 3H), 7.12 (s, 1H), 7.06 (s, 1H), 3.85 (s, 3H), 3.08 (dd, J=7.3, 4.7 Hz, 4H), 1.16 (t, J=7.3 Hz, 6H). HR-ESI-MS m/z for C$_{40}$H$_{34}$NO$_7$S$^-$ calcd: 672.2134 found: 672.1844.

Synthesis of monosulfoVF2.2(OMe).F

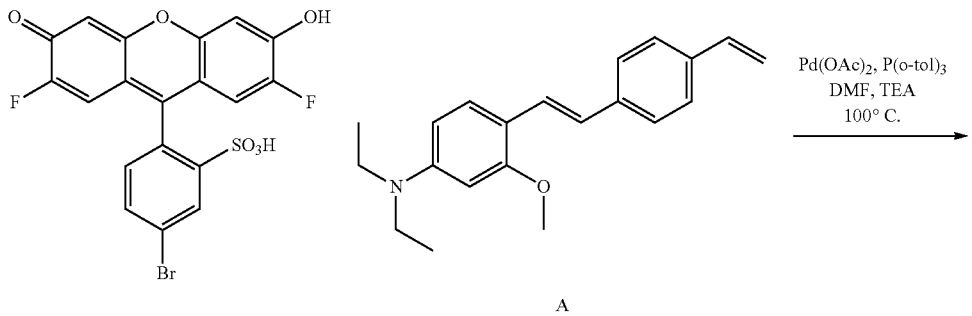

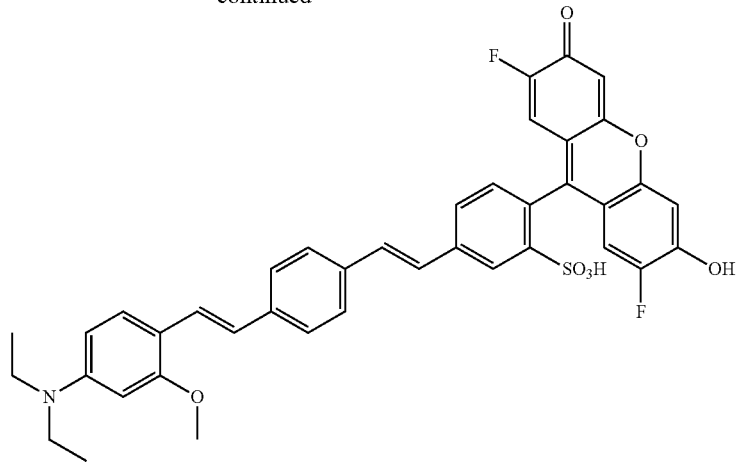

5-bromo-2',7'-difluorosulfofluorescein (100 mg, 0.21 mmol), A (83 mg, 0.25 mmol), palladium acetate (1 mg, 0.045 mmol), and P(o-tol)$_3$ (2.7 mg, 0.09 mmol) were placed in an oven-dried Schlenk flask. The flask was sealed and evacuated/backfilled with nitrogen (3×). Anhydrous DMF (1 mL) and anhydrous Et$_3$N (1 mL) were added via syringe and the reaction was stirred for 16 hours at 100 degrees Celsius. After cooling, the reaction mixture was diluted with 3 mL dichloromethane and filtered through celite, which was then washed with methanol. The solvent was removed from the filtrate via rotary evaporation and the resulting residue was dissolved in 5 mL dichloromethane. The mixture was then poured into diethyl ether, resulting in precipitation of a brown solid. The solid was isolated via vacuum filtration (70 mg, 52%). A small amount of material was purified via RP-HPLC for further characterization. $^1$H NMR (900 MHz, DMSO-d$_6$) δ 8.16 (s, 2H), 7.94 (s, 1H), 7.77 (d, J=9.1 Hz, 2H), 7.72 (s, 1H), 7.69 (s, 1H), 7.65 (d, J=8.1 Hz, 2H), 7.49 (m, 2H), 7.41 (d, J=17.9 Hz, 1H), 7.39-7.32 (m, 4H), 7.21 (d, J=7.8 Hz, 1H), 6.61 (d, J=11.4 Hz, 2H), 3.85 (s, 3H), 3.09 (p, 4.9 Hz, 4H), 1.11 (t, J=6.5 Hz, 6H). $^{13}$C NMR (226 MHz, DMSO) δ 157.99, 157.71, 157.57, 138.31, 129.92, 127.91, 127.54, 127.19, 126.38, 125.92, 125.38, 117.55, 116.23, 114.91, 104.19, 55.25, 45.72, 41.34. HR-ESI-MS m/z for C$_{40}$H$_{32}$F$_2$NO$_7$S$^-$ calcd: 708.1946 found: 708.1898.

Synthesis of monosulfoVF2.2(OMe).Cl

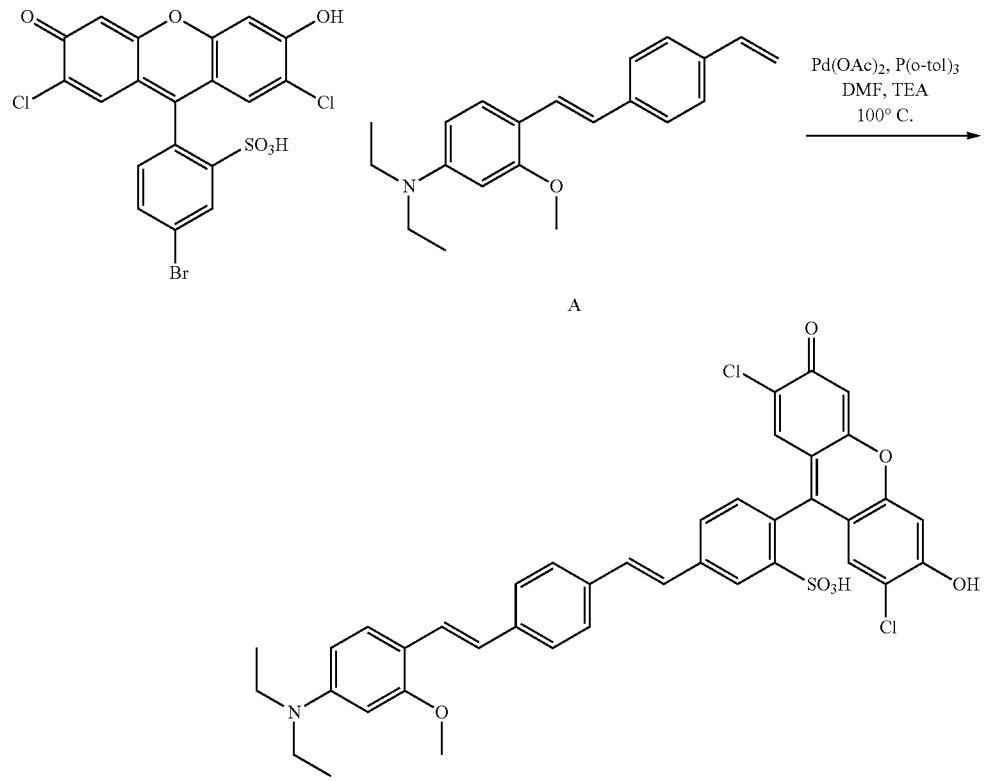

5-bromo-2',7'-dichlorosulfofluorescein (100 mg, 0.19 mmol), A (71 mg, 0.23 mmol), palladium acetate (1 mg, 0.045 mmol), and P(o-tol)$_3$ (2.7 mg, 0.09 mmol) were placed in an oven-dried Schlenk flask. The flask was sealed and evacuated/backfilled with nitrogen (3×). Anhydrous DMF (1 mL) and anhydrous Et$_3$N (1 mL) were added via syringe and the reaction was stirred for 16 hours at 100 degrees Celsius. After cooling, the reaction mixture was diluted with 3 mL dichloromethane and filtered through celite, which was then washed with methanol. The solvent was removed from the filtrate via rotary evaporation and the resulting residue was dissolved in 5 mL dichloromethane. The mixture was then poured into diethyl ether, resulting in precipitation of a brown solid. The solid was isolated via vacuum filtration (55 mg, 46%). A small amount of material was purified via RP-HPLC for further characterization. $^1$H NMR (900 MHz, DMSO-d$_6$) δ 8.22 (s, 2H), 7.71 (d, J=8.1 Hz, 1H), 7.56 (d, J=8.0 Hz, 2H), 7.49 (d, J=16.3 Hz, 1H), 7.45 (d, J=8.4 Hz, 2H), 7.34 (d, J=16.3 Hz, 2H), 7.20 (d, J=16.2 Hz, 1H), 7.15 (s, 1H), 7.07 (m, 1H), 7.00 (d, J=16.5 Hz, 2H), 6.73 (d, J=8.4 Hz, 3H), 3.44 (s, 3H), 3.08 (dd, J=7.2, 4.9 Hz, 4H), 1.16 (t, J=7.3 Hz, 6H). $^{13}$C NMR (226 MHz, DMSO) δ 157.78, 157.64, 157.51, 149.97, 147.92, 127.61, 127.33, 126.16, 125.61, 118.75, 117.84, 116.52, 115.19, 112.28, 112.25, 100.92, 53.33, 45.70. HR-ESI-MS m/z for C$_{40}$H$_{32}$Cl$_2$NO$_7$S$^-$ calcd: 740.1355 found: 740.1322.

Synthesis of disulfoVF2.1.H

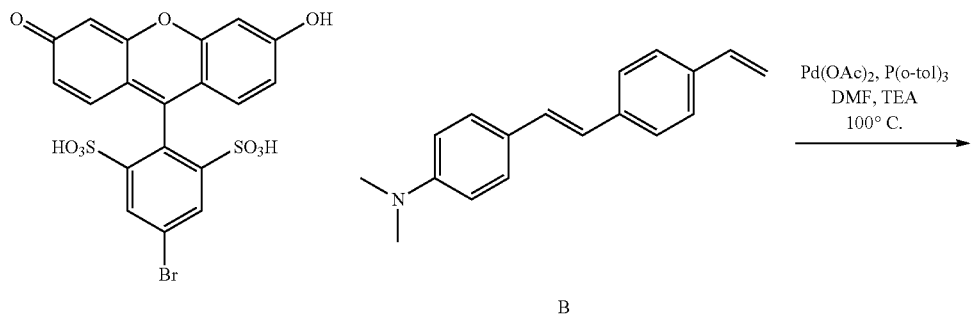

B

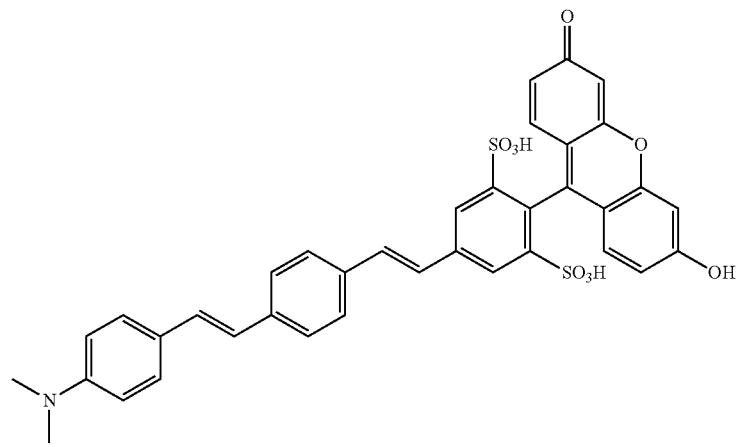

5-bromodisulfofluorescein (100 mg, 0.19 mmol), B (56 mg, 0.22 mmol), palladium acetate (1 mg, 0.045 mmol), and P(o-tol)$_3$ (2.7 mg, 0.09 mmol) were placed in an oven-dried Schlenk flask. The flask was sealed and evacuated/backfilled with nitrogen (3×). Anhydrous DMF (1 mL) and anhydrous Et$_3$N (1 mL) were added via syringe and the reaction was stirred for 16 hours at 100 degrees Celsius. After cooling, the reaction mixture was diluted with 10 mL methanol and filtered through celite, which was then washed with methanol. The solvent was removed from the filtrate via rotary evaporation and the resulting residue was dissolved in 5 mL dichloromethane. The mixture was then poured into diethyl ether, resulting in precipitation of a brown solid. The solid was isolated via vacuum filtration (37 mg, 28%). A small amount of material was purified via RP-HPLC for further characterization. $^1$H NMR (900 MHz, DMSO-d$_6$) δ 8.16 (s, 2H), 8.12 (s, 2H), 7.78 (d, J=7.9 Hz, 2H), 7.64 (d, J=7.8 Hz, 2H), 7.54 (d, J=7.6 2H), 7.50 (d, J=7.9 Hz, 2H), 7.40 (d, J=11.5 Hz, 1H), 7.34 (d, J=16.5 Hz, 1H), 7.24 (d, J=7.7 Hz, 1H), 7.15 (s, 1H), 7.09 (s, 2H), 7.04 (s, 2H), 2.88 (s, 6H). HR-ESI-MS m/z for C$_{37}$H$_{28}$NO$_9$S$_2^-$ calcd: 694.1284 found: 694.1188.

Synthesis of disulfoVF2.1.F

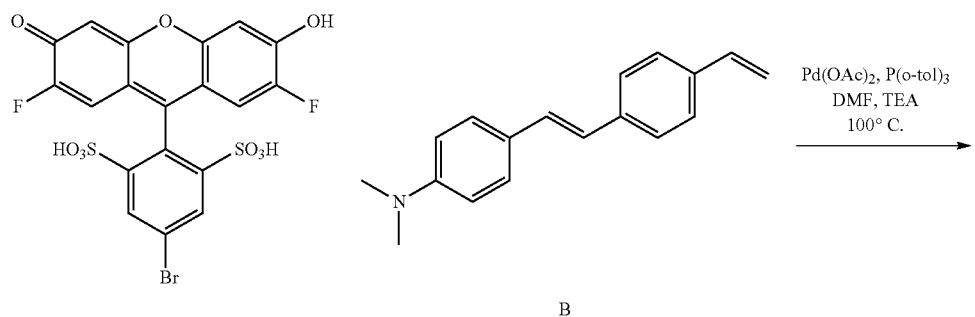

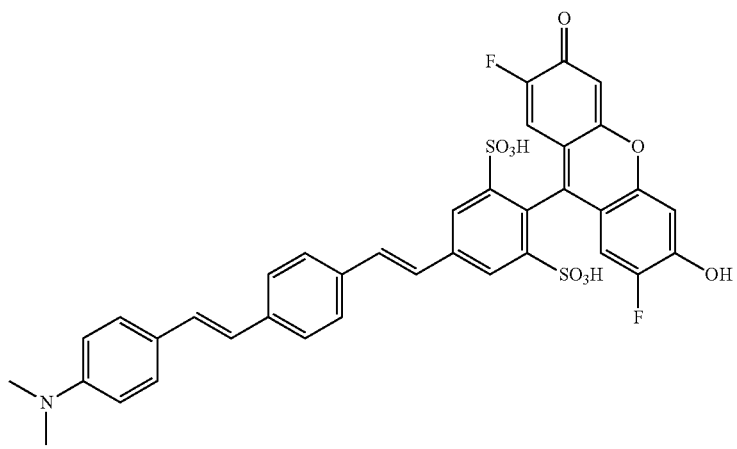

5-bromo-2',7'-difluorodisulfofluorescein (100 mg, 0.19 mmol), B (53 mg, 0.21 mmol), palladium acetate (1 mg, 0.045 mmol), and P(o-tol)$_3$ (2.7 mg, 0.09 mmol) were placed in an oven-dried Schlenk flask. The flask was sealed and evacuated/backfilled with nitrogen (3×). Anhydrous DMF (1 mL) and anhydrous Et$_3$N (1 mL) were added via syringe and the reaction was stirred for 16 hours at 100 degrees Celsius. After cooling, the reaction mixture was diluted with 10 mL methanol and filtered through celite, which was then washed with methanol. The solvent was removed from the filtrate via rotary evaporation and the resulting residue was dissolved in 5 mL dichloromethane. The mixture was then poured into diethyl ether, resulting in precipitation of a brown solid. The solid was isolated via vacuum filtration (30 mg, 23%). A small amount of material was purified via RP-HPLC for further characterization. $^1$H NMR (900 MHz, DMSO-d$_6$) δ 7.73 (s, 2H), 7.70 (d, J=8.4 Hz, 2H), 7.56 (s, 2H), 7.53-7.49 (m, 1H), 7.45 (d, J=9.0 Hz, 4H), 7.30 (d, J=16.5 Hz, 1H), 7.19 (d, J=18.2 Hz, 1H), 7.00 (d, J=15.8 Hz, 1H), 6.98-6.93 (m, 1H), 6.75-6.69 (m, 3H), 2.93 (s, 6H). HR-ESI-MS m/z for C$_{37}$H$_{26}$F$_2$NO$_9$S$_2^-$ calcd: 730.1905 found: 730.1798.

Synthesis of disulfoVF2.1.Cl 5-bromo-2',7'-dichlorodisulfofluorescein (100 mg, 0.17 mmol), B (50 mg, 0.20 mmol), palladium acetate (1 mg, 0.045 mmol), and P(o-tol)$_3$ (2.7 mg, 0.09 mmol) were placed in an oven-dried Schlenk flask. The flask was sealed and evacuated/backfilled with nitrogen (3×). Anhydrous DMF (1 mL) and anhydrous Et$_3$N (1 mL) were added via syringe and the reaction was stirred for 16 hours at 100 degrees Celsius. After cooling, the reaction mixture was diluted with 10 mL methanol and filtered through celite, which was then washed with methanol. The solvent was removed from the filtrate via rotary evaporation and the resulting residue was dissolved in 5 mL dichloromethane. The mixture was then poured into diethyl ether, resulting in precipitation of a brown solid. The solid was isolated via vacuum filtration (48 mg, 38%). A small amount of material was purified via RP-HPLC for further characterization. $^1$H NMR (900 MHz, DMSO-d$_6$) δ 8.35 (s, 2H), 8.03 (s, 2H), 7.80 (d, J=8.2 Hz, 2H), 7.68 (d, J=8.2 Hz, 2H), 7.57 (d, J=8.6 Hz, 2H), 7.54 (d, J=16.2 Hz, 1H), 7.46 (d, J=16.4 Hz, 1H), 7.29 (d, J=16.3 Hz, 1H), 7.11 (d, J=16.2 Hz, 1H), 7.01 (s, 2H), 6.84 (d, J=8.7 Hz, 2H), 3.04 (s, 6H). $^{13}$C NMR (226 MHz, CDCl$_3$) δ 162.99, 152.00, 150.42, 147.99, 138.21, 136.12, 135.25, 130.63, 129.63, 129.41, 128.04, 126.61, 126.21, 125.23, 124.46, 123.48, 112.62, 41.83. HR-ESI-MS m/z for C$_{37}$H$_{26}$F$_2$NO$_9$S$_2^-$ calcd: 762.0504 found: 762.0468.

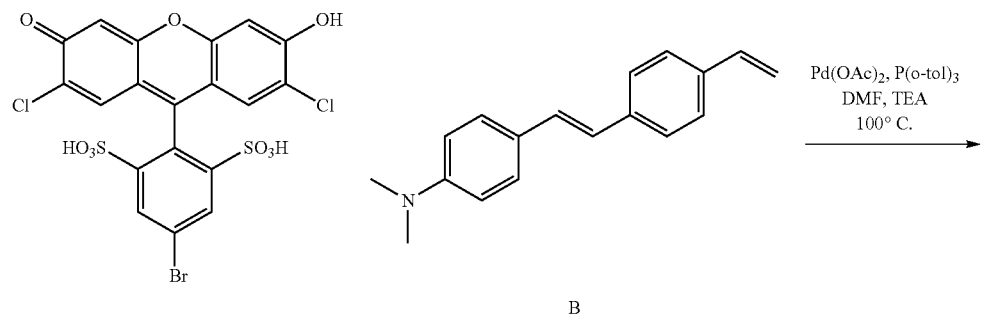

B

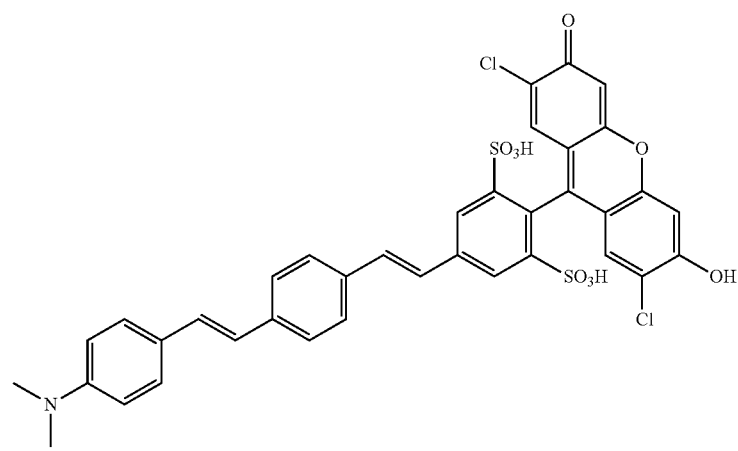

Synthesis of disulfoVF2.2(OMe).H

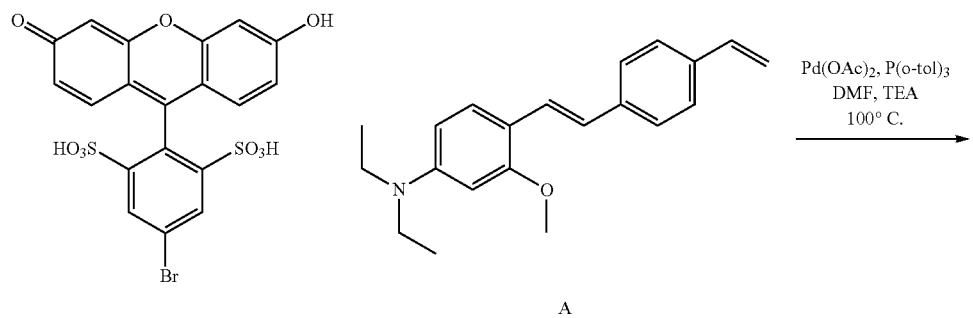

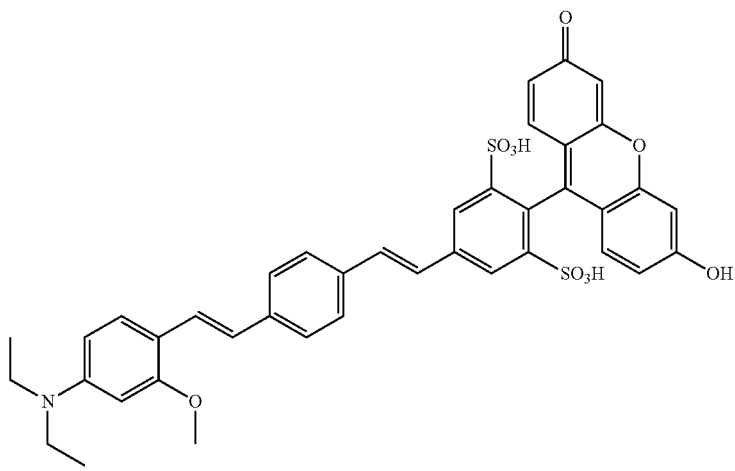

5-bromodisulfofluorescein (100 mg, 0.19 mmol), A (69 mg, 0.23 mmol), palladium acetate (1 mg, 0.045 mmol), and P(o-tol)$_3$ (2.7 mg, 0.09 mmol) were placed in an oven-dried Schlenk flask. The flask was sealed and evacuated/backfilled with nitrogen (3×). Anhydrous DMF (1 mL) and anhydrous Et$_3$N (1 mL) were added via syringe and the reaction was stirred for 16 hours at 100 degrees Celsius. After cooling, the reaction mixture was diluted with 10 mL methanol and filtered through celite, which was then washed with methanol. The solvent was removed from the filtrate via rotary evaporation and the resulting residue was dissolved in 5 mL dichloromethane. The mixture was then poured into diethyl ether, resulting in precipitation of a brown solid. The solid was isolated via vacuum filtration (52 mg, 37%). A small amount of material was purified via RP-HPLC for further characterization. $^1$H NMR (900 MHz, DMSO-d$_6$) δ 8.19 (s, 1H), 7.67 (d, J=7.9 Hz, 2H), 7.60-7.56 (m, 1H), 7.54-7.50 (m, 1H), 7.47 (d, J=7.5 Hz, 1H), 7.46 (s, 1H), 7.44 (s, 1H), 7.34-7.29 (m, 3H), 7.23 (d, J=7.8 Hz, 1H), 7.13 (s, 1H), 6.97 (s, 3H), 6.84 (d, J=9.2 Hz, 1H), 6.52 (s, 2H), 3.82 (s, 3H), 3.06 (dd, J=13.6, 6.3 Hz, 4H), 1.15-1.11 (m, 6H). HR-ESI-MS m/z for C$_{40}$H$_{34}$NO$_{10}$S$_2$$^-$ calcd: 752.1702 found: 752.1684.

Synthesis of disulfoVF2.2(OMe).F

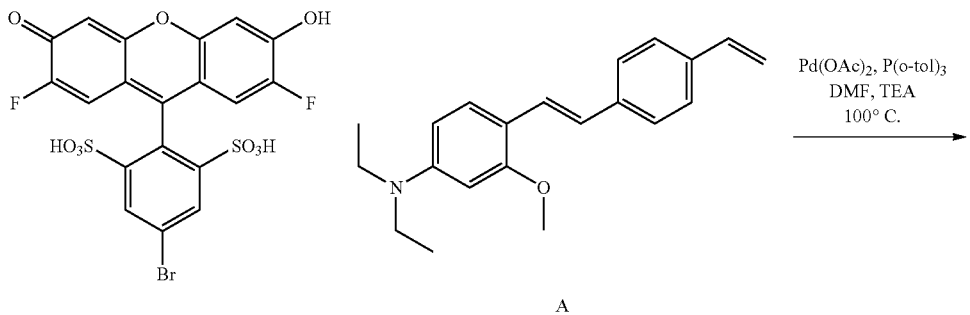

-continued

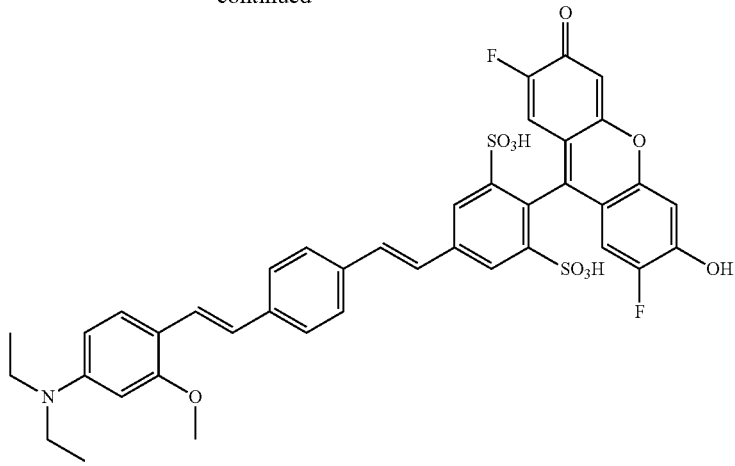

5-bromo-2'7'-difluorodisulfofluorescein (100 mg, 0.18 mmol), A (65 mg, 0.21 mmol), palladium acetate (1 mg, 0.045 mmol), and P(o-tol)$_3$ (2.7 mg, 0.09 mmol) were placed in an oven-dried Schlenk flask. The flask was sealed and evacuated/backfilled with nitrogen (3×). Anhydrous DMF (1 mL) and anhydrous Et$_3$N (1 mL) were added via syringe and the reaction was stirred for 16 hours at 100 degrees Celsius. After cooling, the reaction mixture was diluted with 10 mL methanol and filtered through celite, which was then washed with methanol. The solvent was removed from the filtrate via rotary evaporation and the resulting residue was dissolved in 5 mL dichloromethane. The mixture was then poured into diethyl ether, resulting in precipitation of a brown solid. The solid was isolated via vacuum filtration (79 mg, 56%). A small amount of material was purified via RP-HPLC for further characterization. $^1$H NMR (900 MHz, DMSO-d$_6$) δ 8.22 (s, 2H), 8.17 (s, 1H), 8.12 (s, 1H), 7.68 (d, J=7.8 Hz, 2H), 7.50-7.47 (m, 2H), 7.47-7.40 (m, 1H), 7.34 (d, J=16.4 Hz, 1H), 7.29 (d, J=16.6 Hz, 1H), 7.09 (m, 1H), 7.03-6.95 (m, 1H), 6.30 (s, 1H), 6.22 (s, 1H), 3.85 (s, 3H), 3.09 (dd, J=7.3, 5.0 Hz, 4H), 1.17 (t, J=7.3 Hz, 6H). HR-ESI-MS m/z for C$_{40}$H$_{32}$F$_2$NO$_{10}$S$_2^-$ calcd: 788.1514 found: 788.1394.

Synthesis of disulfoVF2.2(OMe).Cl

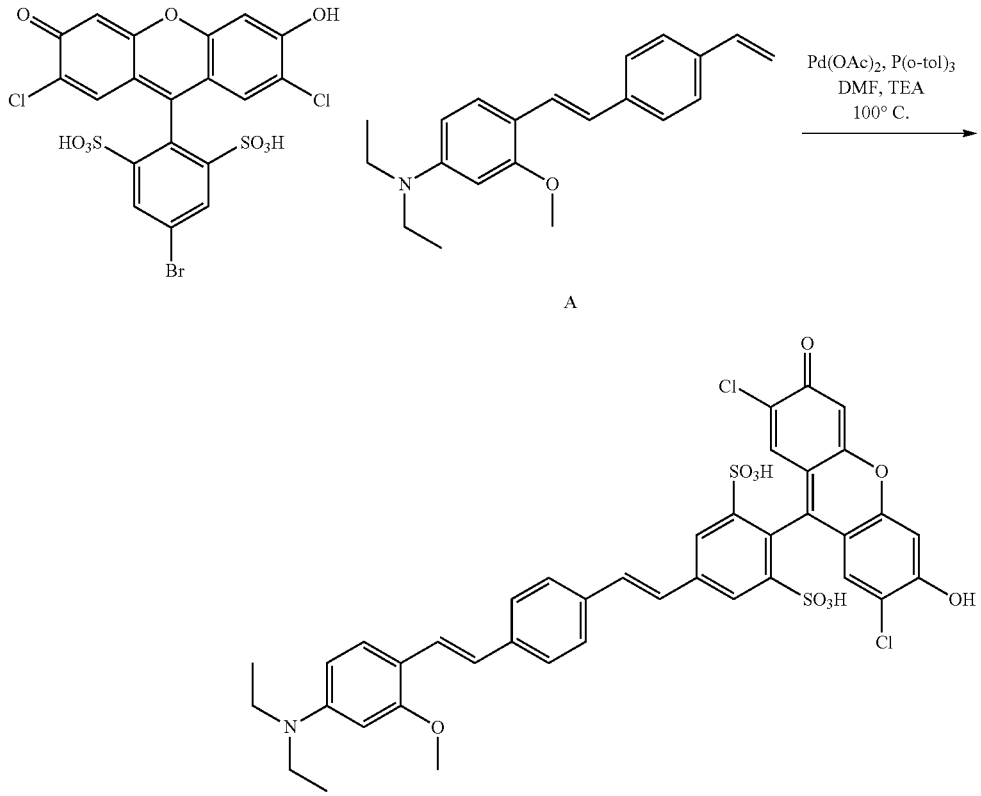

5-bromo-2'7'-dichlorodisulfofluorescein (100 mg, 0.18 mmol), A (65 mg, 0.21 mmol), palladium acetate (1 mg, 0.045 mmol), and P(o-tol)$_3$ (2.7 mg, 0.09 mmol) were placed in an oven-dried Schlenk flask. The flask was sealed and evacuated/backfilled with nitrogen (3×). Anhydrous DMF (1 mL) and anhydrous Et$_3$N (1 mL) were added via syringe and the reaction was stirred for 16 hours at 100 degrees Celsius. After cooling, the reaction mixture was diluted with 10 mL methanol and filtered through celite, which was then washed with methanol. The solvent was removed from the filtrate via rotary evaporation and the resulting residue was dissolved in 5 mL dichloromethane. The mixture was then poured into diethyl ether, resulting in precipitation of a brown solid. The solid was isolated via vacuum filtration (79 mg, 56%). A small amount of material was purified via RP-HPLC for further characterization. $^1$H NMR (900 MHz, DMSO-d$_6$) δ 8.24 (s, 1H), 7.95 (d, J=8.1 Hz, 2H), 7.93-7.89 (m, 2H), 7.69 (d, J=16.4 Hz, 2H), 7.43 (d, J=16.4 Hz, 2H), 7.11 (s, 2H), 7.05 (s, 1H), 7.00 (s, 1H), 6.85 (s, 1H), 6.75 (s, 2H), 6.61 (s, 1H), 3.83 (s, 3H), 3.08-3.03 (m, 4H), 1.13 (t, J=7.4 Hz, 6H). $^{13}$C NMR (226 MHz, DMSO) δ 192.94, 162.75, 158.44, 148.62, 143.30, 137.41, 135.74, 131.61, 131.36, 130.43, 130.16, 130.09, 129.37, 127.92, 126.74, 118.54, 118.04, 117.62, 116.31, 115.00, 102.93, 46.17, 41.80, 36.22, 34.80, 31.21. HR-ESI-MS m/z for $C_{40}H_{32}Cl_2NO_{10}S_2^-$ calcd: 820.0923 found: 819.9684.

Differentiation of mDA Neurons.

mDA neurons were derived from H1 human embryonic stem cells (hESCs) using medium conditions as described in Kriks et al., Nature, 480, 547, 2011). On Day 25 of differentiation, cells were harvested from the culture platform and pipetted to generate small 50-100 μm clusters, and seeded on 12 mm glass coverslips coated with 20 μg/ml Laminin (ThermoFischer Scientific). Cells were subsequently matured for 10 days before voltage sensitive imaging.

Voltage Sensitivity in HEK Cells.

Functional imaging of VF dyes was performed using a 20× objective paired with image capture from the EMCCD camera at a sampling rate of 0.5 kHz. VF dyes were excited using the 488 nm LED with an intensity of 2.5 W/cm$^2$. For initial voltage characterization emission was collected with the QUAD filter (430/32, 508/14, 586/30, 708/98 nm) after passing through a quadruple dichroic mirror (432/38, 509/22, 586/40, 654 nm LP).

Voltage Imaging of Neurons.

Functional imaging of mDA cells was performed using a 20× objective paired with image capture from the ORCA-Flash4.0 camera (Hamamatsu) at a sampling rate of 100 Hz. VoltageFluor dye was excited using the 488 nm LED with an intensity of 2.5 W/cm$^2$. Light was collected with the QUAD filter (430/32, 508/14, 586/30, 708/98 nm) after passing through a quadruple dichroic mirror (432/38, 509/22, 586/40, 654 nm LP). For image analysis, a custom Matlab routine was employed. Briefly, a TIFF stack was imported into Matlab and the intensity values a user-designated block of pixels was extracted as an array. The intensity over time for each block was then baseline corrected by fitting to a 2nd degree polynomial. Cells were selected by drawing regions of interest around cells in a DIC image corresponding to the video, outputting the bleach-corrected trace as an Excel file and spike times (frames in which the intensity was greater than 3× the standard deviation of the overall trace) as a text file.

Determination of Photostability.

HEK cells were incubated separately with ms- and ds-VF2.1.Cl and VF2.2(OMe). Cl at 1 μM in HBSS at 37 degrees Celsius for 15 minutes. Data were acquired with a W-Plan-Apo 63×/1.0 objective (Zeiss) and the ORCA-Flash4.0 camera (Hamamatsu). Images were exposed for 10 milliseconds each across 50 seconds with a constant illumination of the 488 nm LED (153 W/cm$^2$). The excitation light was collected with the QUAD filter (430/32, 508/14, 586/30, 708/98 nm) after passing through a quadruple dichroic mirror (432/38, 509/22, 586/40, 654 nm LP). The fluorescence curves were background subtracted and then normalized to the fluorescence intensity at t=0 and averaged across five cells of each dye.

Electrophysiology.

For electrophysiological experiments, pipettes were pulled from borosilicate glass (Sutter Instruments, BF150-86-10), with a resistance of 5-8 MΩ, and were filled with an internal solution; (in mM) 115 potassium gluconate, 10 BAPTA tetrapotassium salt, 10 HEPES, 5 NaCl, 10 KCl, 2 ATP disodium salt, 0.3 GTP trisodium salt (pH 7.25, 275 mOsm).

Recordings were obtained with an Axopatch 200B amplifier (Molecular Devices) at room temperature. The signals were digitized with Digidata 1332A, sampled at 50 kHz and recorded with pCLAMP 10 software (Molecular Devices) on a PC. Fast capacitance was compensated in the on-cell configuration. For all electrophysiology experiments, recordings were only pursued if series resistance in voltage clamp was less than 30 MΩ. For whole-cell, voltage clamp recordings in HEK 293T cells, cells were held at −60 mV and 100 ms hyper- and depolarizing steps applied from −100 to +100 mV in 20 mV increments. For whole-cell, following membrane rupture, resting membrane potential was assessed and recorded at I=0 and monitored during the data acquisition.

Image Analysis.

Analysis of voltage sensitivity in HEK cells was performed using custom Matlab routines. Briefly, a region of interest (ROI) was selected automatically based on fluorescence intensity and applied as a mask to all image frames. Fluorescence intensity values were calculated at known baseline and voltage step epochs.

Solubility of VoltageFluor Dyes.

Suspensions of 5 milligrams each of solid mono- and disulfo-dichlorofluoresceins in 5 mL of distilled water were created. Over the course of three days, 5 milligrams of solid material was added at a time, ensuring that no visible particulates were present in the solution prior to addition. At the end of the experiment, the suspension was filtered through filter paper and then through a 0.22-μm polytetrafluoroethylene filter into a scintillation vial. 10 μL of this filtrate was used as a stock solution to determine the concentration of fluorescein present via UV-Vis spectrophotometry and the remainder was lyophilized and the amount of solid resulting was measured using an analytical microbalance. For VF dyes (VF2.1.Cl and VF2.2(OMe).Cl, both ms and ds versions), saturated solutions in distilled water were prepared via dilution from a 100 μM stock in DMSO for a resulting solution containing 0.1% DMSO. The solutions were allowed to sit overnight at 20 degrees Celsius and then filtered through 0.22-μm filters. The resulting filtrates were used as stock solutions to determine the amount of VF present via UV-Vis spectrophotometry.

Molecular Dynamics Simulation Parameters and Protocols.

Figure 1B:
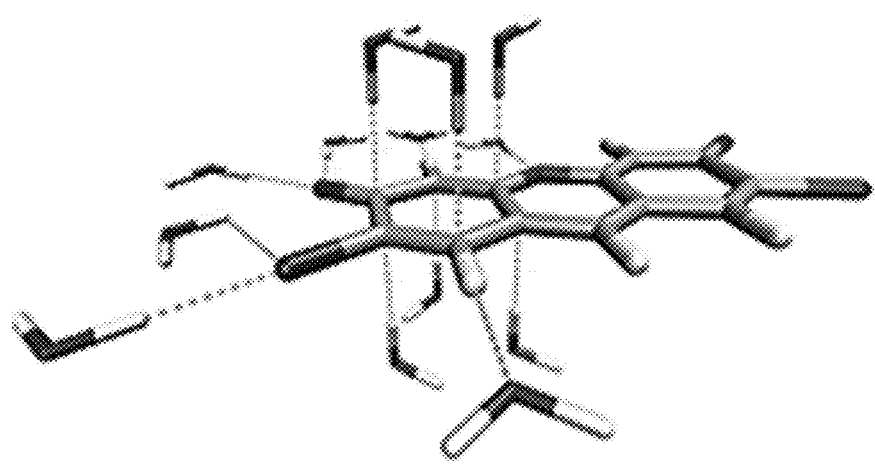
Figure 1C:
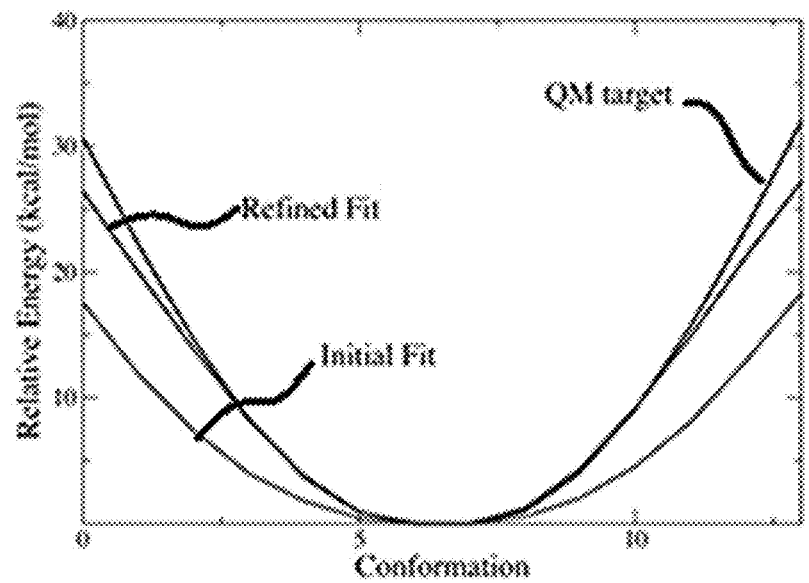

The msVF and dsVF molecules were parameterized in CHARMM General force field (CGenFF). The CGenFF program was used to obtain initial parameters, which were subsequently optimized with the Force Field Toolkit (fftk) and the program Gaussian 09. Briefly, an entire VF molecule is divided into four parts during the parameterization (FIG. 1). As benzenesulfonate and N,N-dimethylaniline were already in the CHARMM general force field, only the remaining two parts (xanthene derivative and (E)-stilbene) were submitted to the CGenFF program. Based on the resulting penalty scores, two dihedrals in (E)-stilbene were selected and optimized via fftk and Gaussian 09. For the −1 charged xanthene derivative, its atom typing and initial charge assignment was not based on the CGenFF program output. Instead, we first performed its geometry optimization at the MP2/6-31+G* level via Gaussian 09, which confirmed a symmetric and planar structure of the tricyclic ring. Atom type and initial charges were then assigned for the xanthene derivative based on the compounds phenoxazine, phenoxide and chlorobenzene from the CHARMM general force field and performed charge and dihedral optimization (FIG. 1).

MD simulation system with either a msVF or a dsVF molecule was constructed by inserting it vertically inside the upper monolayer of a POPC bilayer, which was previously equilibrated in a 1-μs simulation performed on the specialized machine Anton. In each system, one lipid molecule overlapping with the inserted msVF or dsVF was removed. Using the autoionize plugin of VMD, the systems were neutralized by adding sodium and chloride ions at a concentration of 0.1 mol/L. Final simulation systems contain ~46,000 atoms, with a size of approximately 75×75×73 Å$^3$. Three replicas of ~500 ns simulations were performed to examine the orientation of msVF in the POPC bilayer, while three replicas of ~200 ns simulations were performed for the dsVF molecule in POPC. The longer simulation time for the former VF molecule is chosen based on its longer correlation time shown in FIG. 2.

All simulations were performed with the 2.10 release of NAMD and the CHARMM36 force field for lipids as well as the CGenFF force field. A time step of 2 fs was adopted in all simulations, with bonds involving hydrogen atoms constrained using RATTLE and water geometries maintained using SETTLE. The multiple-time-stepping algorithm was used, with short-range forces calculated every step and long-range electrostatics calculated every two steps. The cutoff for short-range nonbonded interactions was set to 12 Å, with a switching distance of 10 Å. The CHARMM force switching was used for vdW forces, in order to be consistent with the CHARMM36 force field for lipids. Assuming periodic boundary conditions, the Particle Mesh Ewald (PME) method with a grid density of at least 1/Å$^3$ was employed for computation of long-range electrostatic forces. Langevin dynamics with a damping coefficient of 1 ps$^{-1}$ was used to keep the temperature constant at 310 K, while a Nosé-Hoover-Langevin piston was used to keep the pressure constant at 1 atm. The pressure control was performed semi-isotropically: the z axis of the simulation box, which is normal to the membrane, was allowed to fluctuate independently from the x and y axes.

Figure 2:
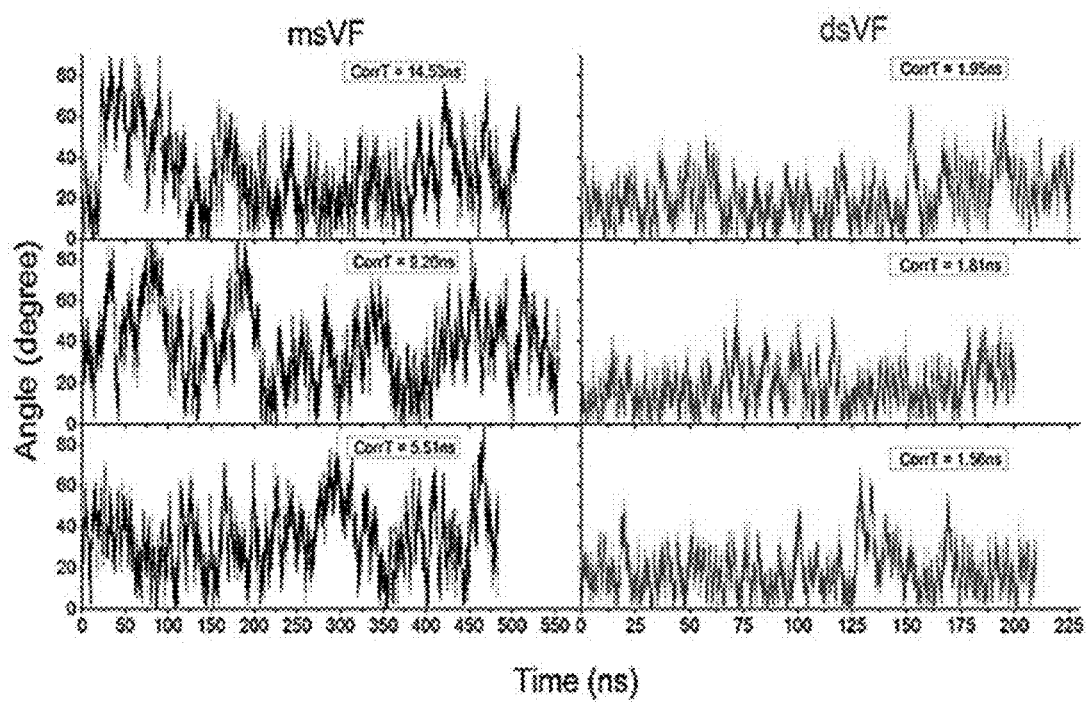
FIG. 2 shows time traces of the tilt angle measured from the three replicas of msVF (left) and dsVF (right) simulations. The correlation time (corrT) of the angle as determined from each simulation is labeled.
Figure 3D:
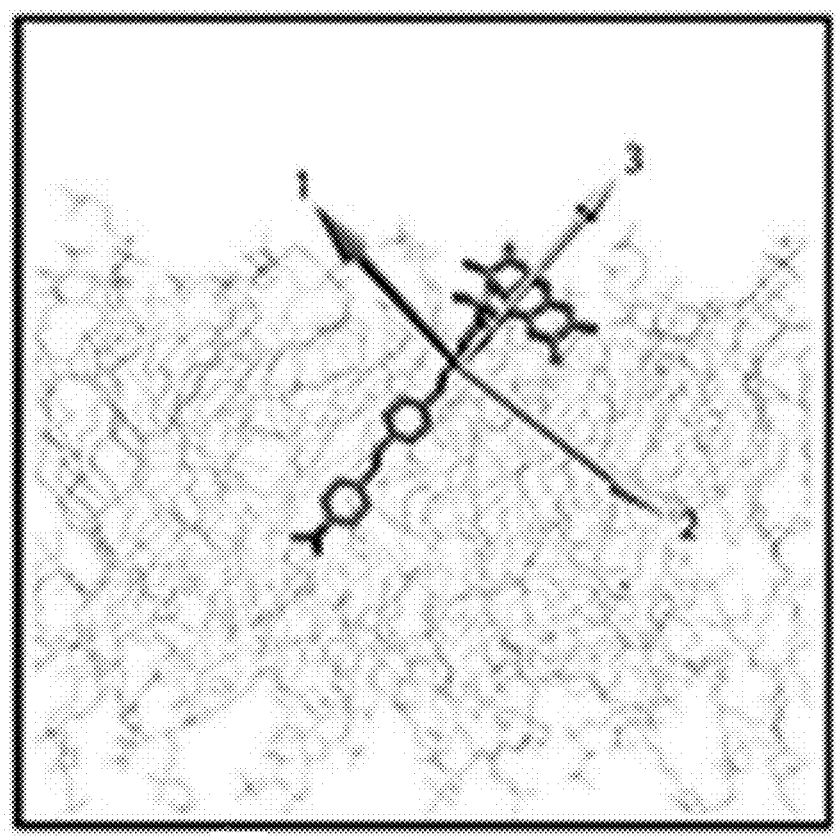
Figure 3E:
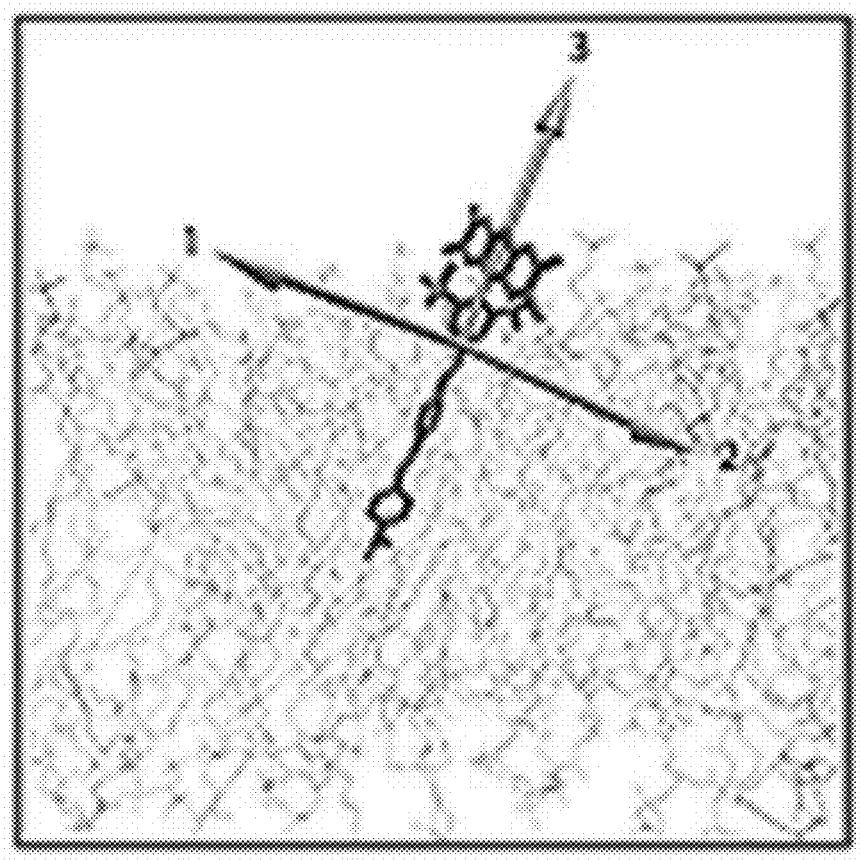

VF2.1.Cl was parameterized with the CHARM general force field (see FIG. 1) and then molecular dynamics (MD) simulations of the VF dye embedded in a 1-palmitoyl-2-oleoyl-sn-glycero-3-phosphocholine (POPC) lipid bilayer was performed, as a simplified model of a mammalian cell membrane. By modeling the behavior of VF2.1.Cl in a POPC lipid bilayer, observations could be made regarding the tilt angle and proposed structural modifications that could then be used to synthesize and assess changes in voltage sensitivity. Three replicates of ~500 ns molecular dynamics simulations of VF2.1.Cl in a pure POPC membrane were performed and the til angle, θ, sampled (between the long axis of VF and the membrane normal) every 5 ps via principle component analysis (PCA). As shown in FIG. 3d, the 2' sulfonate of VF2.1.Cl localized primarily at the lipid:water interface, presumably to avoid burying the charged sulfonate in the non-polar lipid groups. Because the sulfonate of VF2.1.Cl is unsymmetrically positioned off the main axis of VF2.1.Cl, this results in a considerable tilt, with an average angle of 35° (FIGS. 3d and f). Furthermore, the molecule appeared to be rather "floppy" in the membrane, with a standard deviation in the tilt angle of 17° (FIG. 3f) and a correlation time of 9.7 ns (±2.6 ns, ±SEM, n=3 simulations) (FIG. 2). An average tilt angle of 35° implies that the voltage sensitivity of VF2.1.Cl is only about 82% (cosine of 35°) of the theoretical maximum, assuming q and r remain the same.

The tilt angle of the VF dye could be reduced in a straightforward manner by adding a second sulfonate group in the ortho-position on the meso-aryl ring of the xanthene chromophore (FIG. 3A-C). It was postulated that the doubly-sulfonated, disulfoVF dyes (dsVF), with two opposing sulfonate groups at the 2'- and 6'-positions, would have both reduced overall tilt angle and increased rigidity since exposing one sulfonate to bulk water via tilting the whole molecule would require the other sulfonate to become buried in the non-polar lipid layer. Overall, it was hypothesized that smaller fluctuations in the tilt angle of dsVF would cause an improvement in voltage sensitivity relative to monosulfoVF dyes (msVF).

Figure 3F:
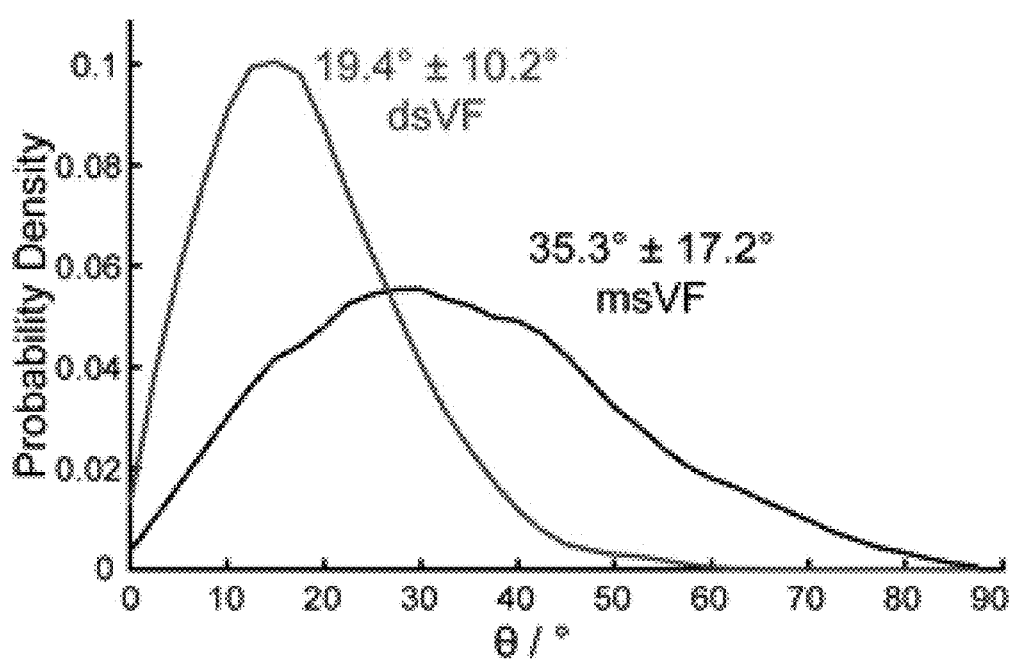

MD simulations were used to test whether the proposed dsVF dye displays enhanced alignment within a model membrane relative to its monosulfo counterpart. MD simulations of dsVF2.1.Cl (FIG. 3d-e) reveal a significant reduction in the tilt angle, θ, compared to msVF2.1.Cl: 19°±10° for dsVF2.1.Cl and 35°±17° for msVF2.1.Cl (FIG. 3f). Compared to msVF, dsVF displays less conformational flexibility within the lipid bilayer, as reflected in the smaller standard deviation of θ values for dsVF2.1.Cl (10° for dsVF vs. 17° for msVF). Analysis of the correlation time for msVF2.1.Cl reveals a much longer periodicity in θ fluctuations (9.7±2.7 ns; ±SEM, n=3 simulations) with larger magnitude swings away from the average orientation (FIG. 2). In contrast, dsVF2.1.Cl has a much shorter period (1.8±0.1 ns; ±SEM, n=3 simulations) characterized by smaller fluctuations in the average angle of displacement (FIG. 2b).

Figure 4A:
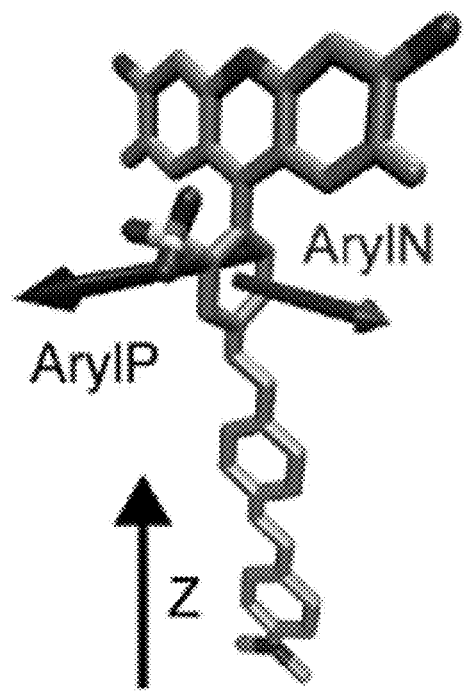
FIG. 4A-E shows calculated orientation of msVF and dsVF in a POPC lipid bilayer. (A) Definition of vectors used to examine angles in VF dyes. "ArylP" describes the vector parallel to the meso-aryl ring; "ArylN" describes the vector normal to the plane of the aryl ring; and "Z" is the membrane normal. Contour plots describe the the ArylP vs Z and ArylN vs Z dihedral angles for a given snapshot of the simulation for (B) msVF and (C) dsVF. The dotted lines serve as a visual guide for a perfect 90° orientation between the dye and the membrane normal. The distribution of dihedral angles sampled during a simulation for (D) ArylP vs Z and (E) ArylN vs Z are plotted for both msVF and dsVF.
Figure 4B:
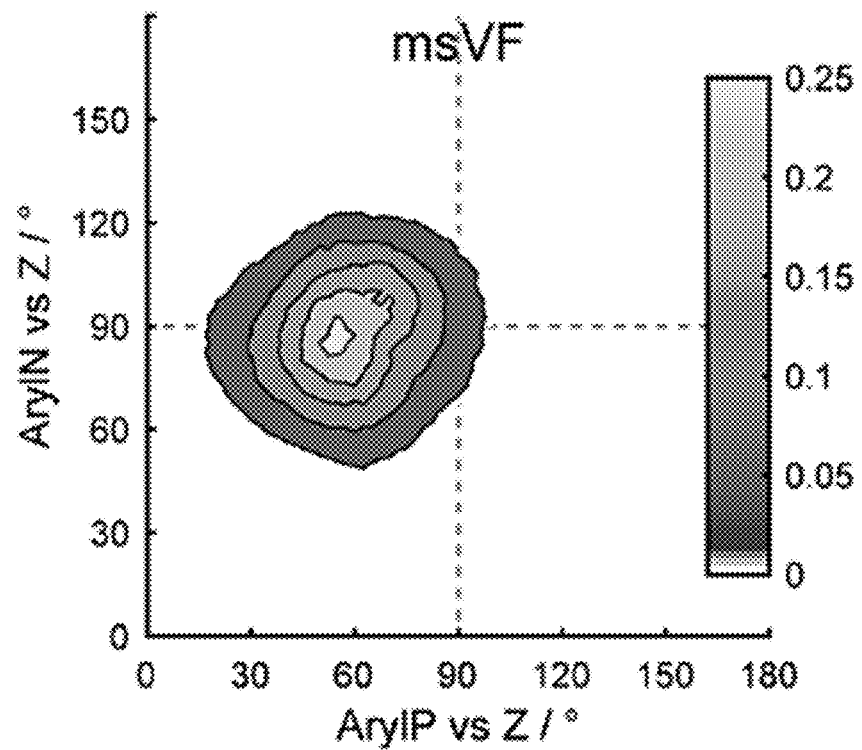
Figure 4C:
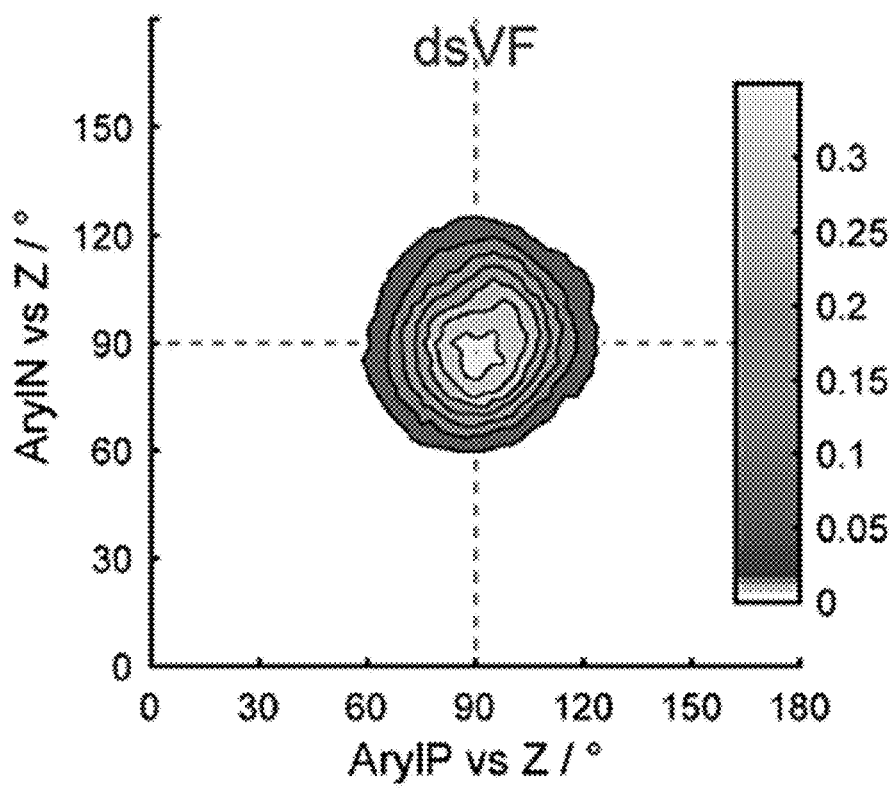
Figure 4D:
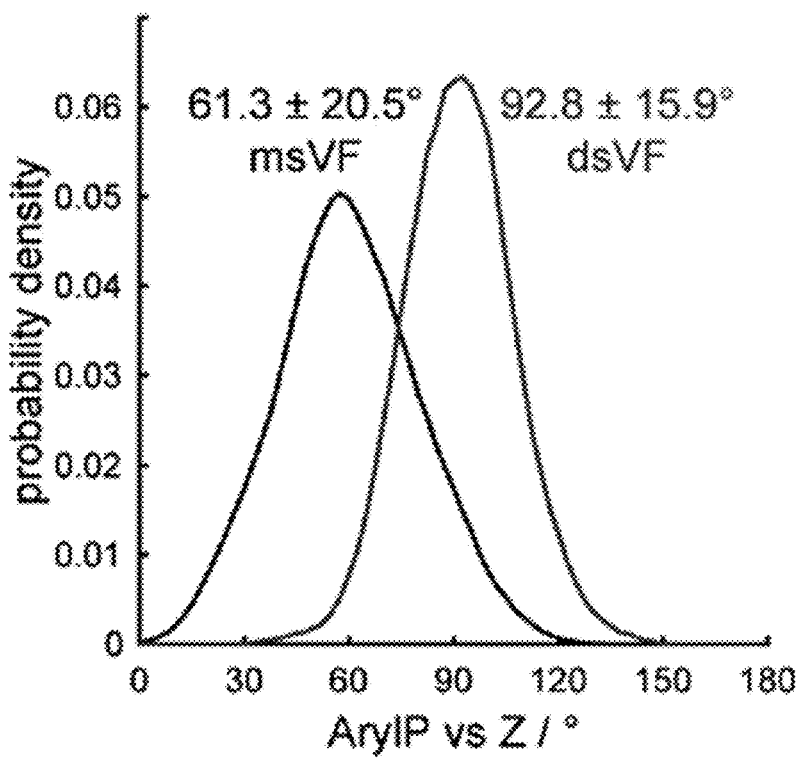
Figure 4E:
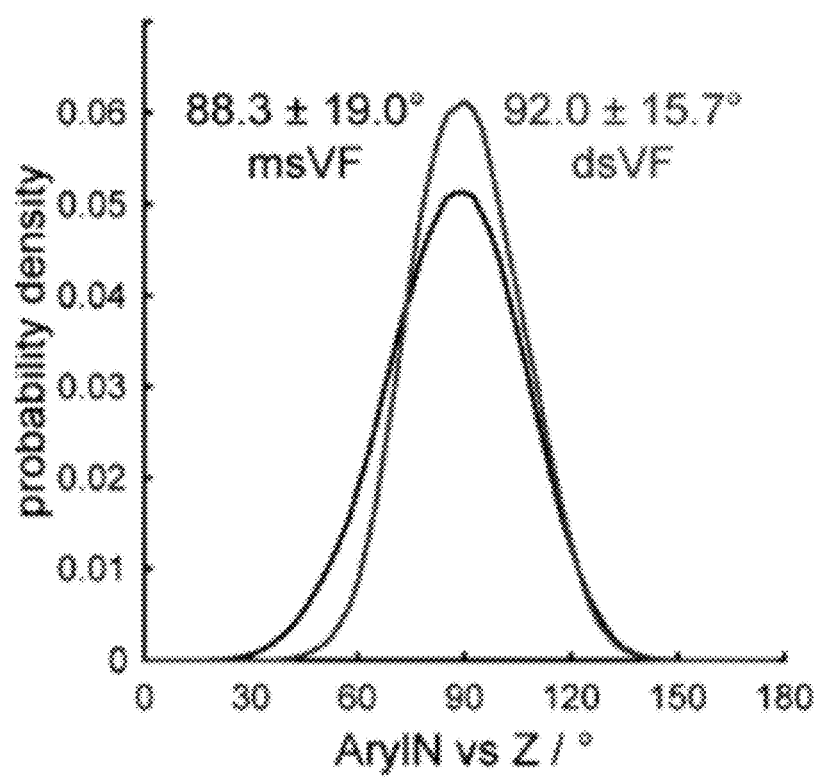

The increased rigidity of the dsVF dye comes primarily from a restriction in the movement of the dye in a single plane. Molecular orientation in the plane of the sulfonates (defined as the angle between the vector parallel to the meso ring system, "ArylP," and the membrane normal "Z" (FIG. 4a) becomes more rigid upon going from msVF (61.3°) to dsVF (92.8°) (FIG. 4b-d). In contrast, motion in the plane perpendicular to the sulfonates (defined as the angle between the vector normal to the meso ring system, "ArylN" and the membrane normal, FIG. 4a) is relatively unchanged, shifting from 88.3° for msVF2.1.Cl to 92.0° for dsVF2.1.Cl (FIGS. 4b-c and e). This is consistent with the hypothesis that symmetric sulfonation rigidifies VF dyes in the plane parallel to the meso aromatic ring, ArylP, but has little effect on motion in the orthogonal coordinate, ArylN (FIG. 4b-c).

Based on the MD simulations, we estimate an approximate 16% increase in voltage sensitivity upon going from a msVF to dsVF dye scaffold, if molecular orientation, or θ, is the only change. This improvement represents a critical increase in the sensitivity of VF-type dyes. According to Equation 3, for a given msVF/dsVF pair, the change in voltage sensitivity should be proportional to the ratio between the cosine of θ for msVF and dsVF.

$$\frac{\Delta F/F_{dsVF}}{\Delta F/F_{msVF}} \propto \frac{\cos\theta_{dsVF}}{\cos\theta_{msVF}} \quad (3)$$

Therefore, a change in θ from 35.4° to 19.4° should give a 16% increase in voltage sensitivity (cosine of 19.4°/cosine of 35.4°=1.157).

To confirm the MD simulation results and experimentally test the hypothesis that improved orientation produces an increase in voltage sensitivity, 6 new doubly-sulfonated VF dyes were synthesized and characterized. Although the chromophores required for msVF are accessible via sulfonic acid anhydrides, generation of the doubly-sulfonated precursors represented a synthetic challenge. To circumvent this problem, a synthesis route was developed from commercially available fluorobenzaldehydes (1 and 2) (see, FIG. 5) that enabled access to both singly and doubly sulfonated dye precursors. Sulfonated halobenzaldehydes 3 and 4 could be prepared via nucleophilic aromatic substitution ($S_NAr$) with sodium sulfite/bisulfite, enabling the bypassing of both the deactivating nature of the sulfonate group and any challenges in directing the sulfonate substitution pattern. Both 5-bromo-2-formyl-benzenesulfonic acid 3 and 5-bromo-2-formyl-1,3-benzenedisulfonic acid 4 were prepared in good yields (64-96%) on the gram scale from commercially available 4-bromo-mono- and di-fluorobenzaldehydes via $S_NAr$ with sodium sulfite/bisulfite in a mixture of water and ethanol.

Figure 5:
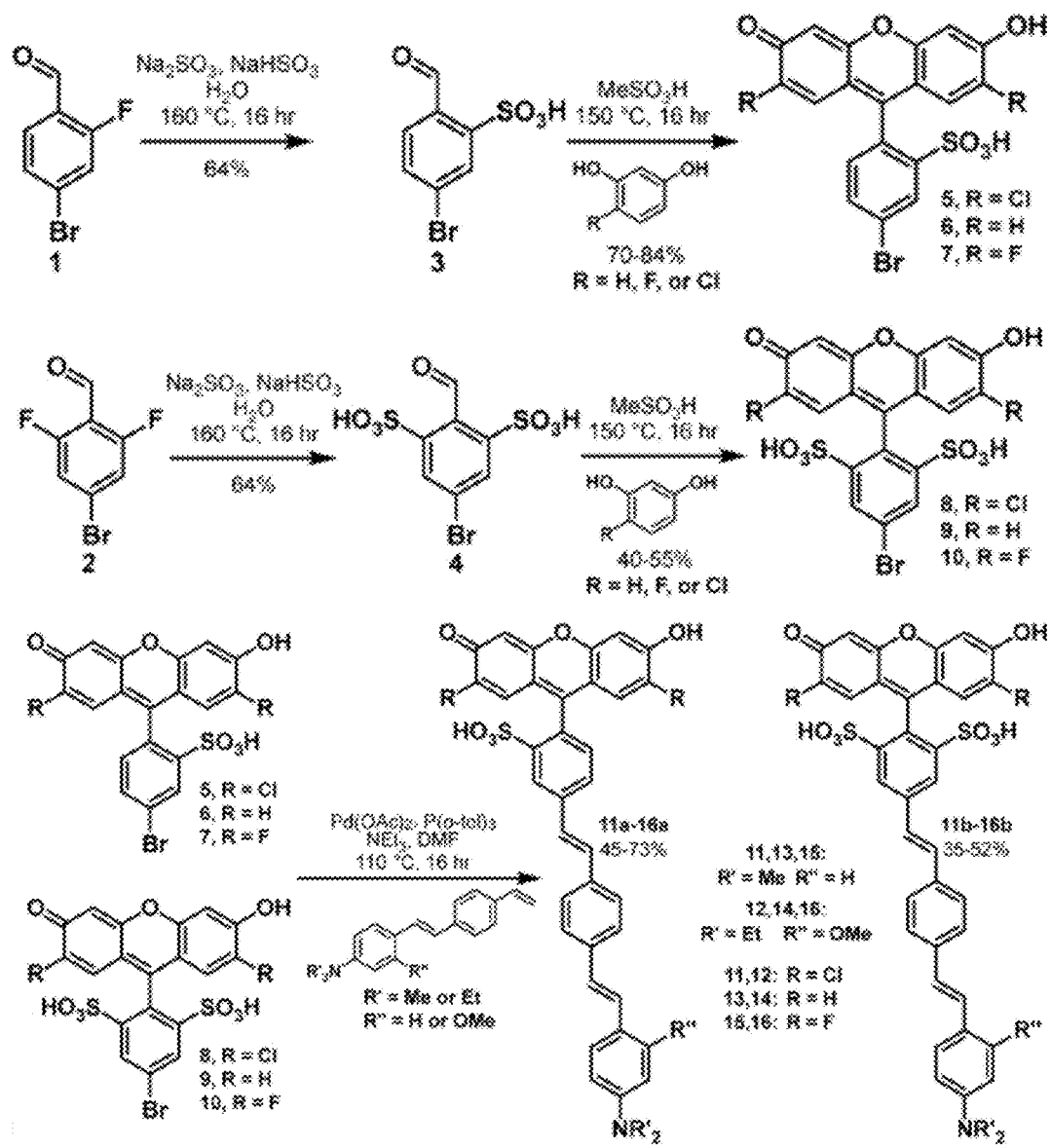
FIG. 5 shows a synthesis route for VF dyes.
Figures 6A, 6B, 6C:
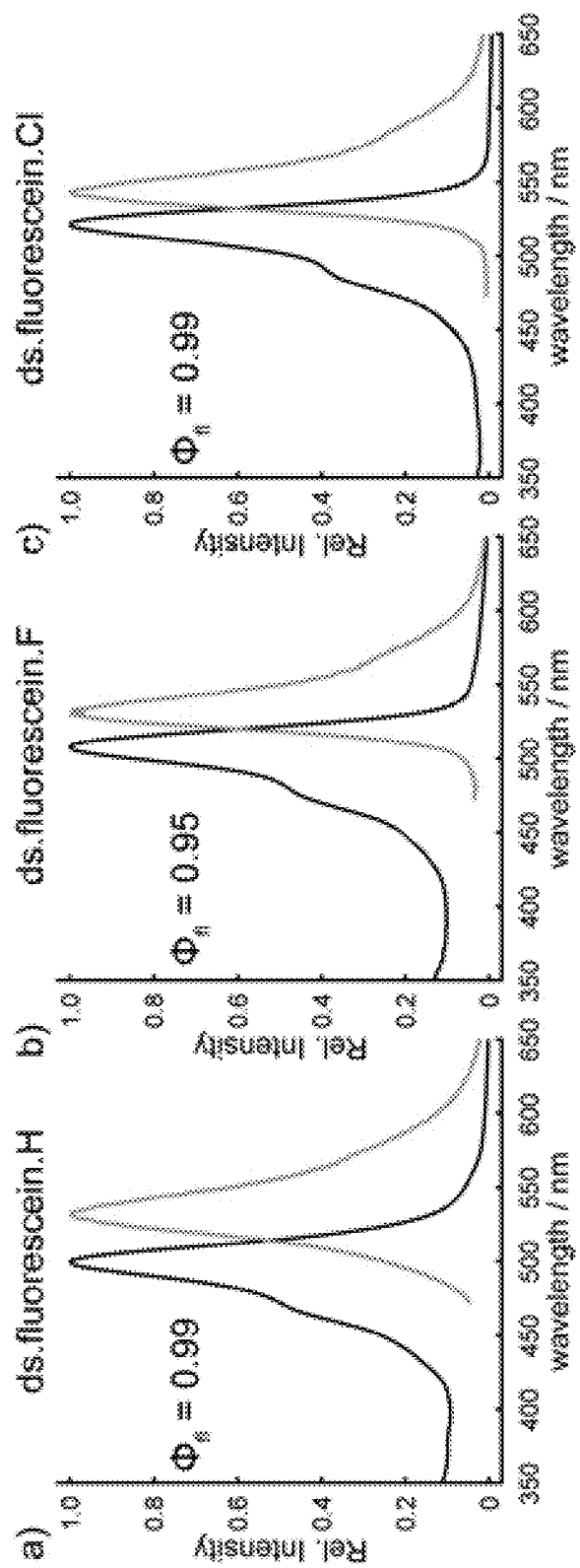
FIG. 6A-C shows Absorption and emission spectra for disulfofluoresceins. Spectra were acquired in phosphate-buffered saline, pH 7.4+0.1% Triton X-100.
Figure 7A:
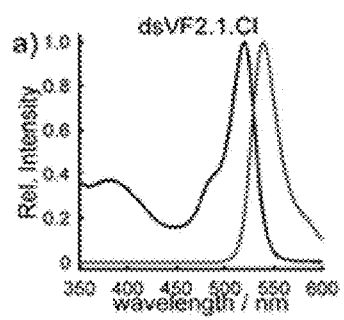
FIG. 7A-I shows Absorption and emission spectra for msVF and dsVF dyes obtained in phosphate-buffered saline, pH 7.4+0.1% Triton X-100 as a surfactant.
Figure 7B:
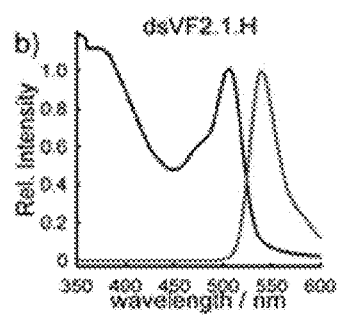
Figure 7C:
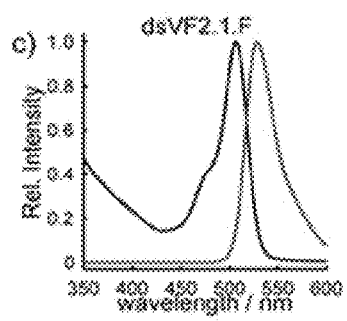
Figure 7D:
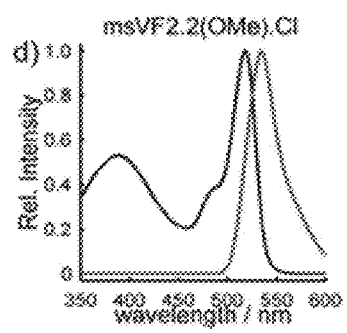
Figure 7E:
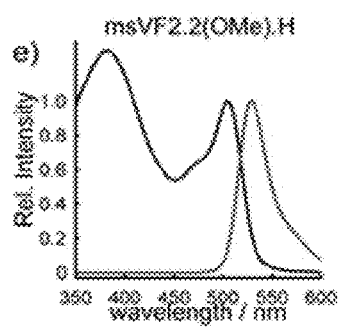
Figure 7F:
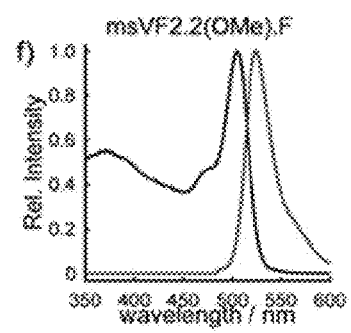
Figure 7G:
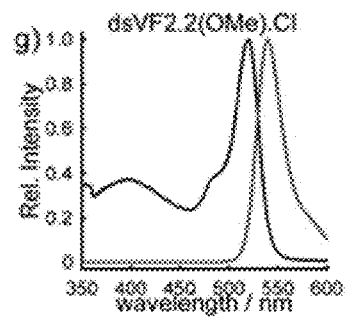
Figure 7H:
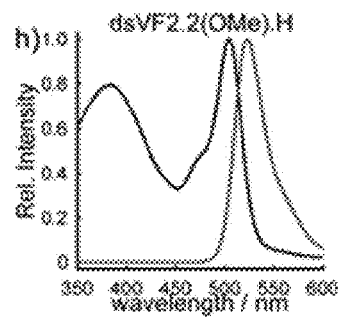
Figure 7I:
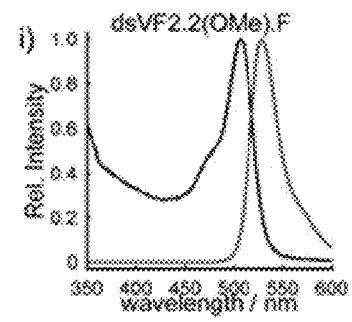

These aldehydes then condensed smoothly with unsubstituted and halogenated resorcinols in methanesulfonic acid (with in situ oxidation by air) to give an array of monosulfonated and disulfonated fluoresceins (5-10), with yields ranging from 40-84% (FIG. 5). Generally, yields of monosulfo-fluoresceins (70-84%) were higher than for corresponding disulfo-fluoresceins (40-55%), which was attributed to the increased steric congestion of disulfo- vs. monosulfobenzaldehydes. The disulfo-fluoresceins show absorption and emission profiles similar to their mono-sulfo counterparts and display high fluorescence quantum yields (near unity, FIG. 6A-C) and aqueous solubility: up to 0.94 mM in $H_2O$ with 0.1% DMSO for ds-dichlorofluorescein vs. only 0.41 mM for ms-dichlorofluorescein.

Methoxy-substituted anilines generally give the best voltage sensitivity in the context of a fluorescein-based voltage sensor, thus, both 3-methoxy and unsubstituted aniline molecular wires were made to test if straightening via double sulfonation is a generalizable strategy. Either a dimethyl aniline molecule wire or a N,N-diethyl-3-methoxyaniline wire were used as the two molecular wire scaffolds in this study. The N,N-diethyl-3-methoxyaniline was used in place of the previously described N,N-dimethyl-3-methoxyaniline wire because the diethyl derivative can be simply prepared from commercially available N,N-diethyl-salicylaldehyde. Heck coupling between the styrene molecular wires and corresponding mono- or di-sulfonated fluoresceins provided the ms- and dsVF dyes after purification via crystallization. Small amounts of dye were purified by semi-preparative HPLC for further analysis.

Figures 8A, 8B:
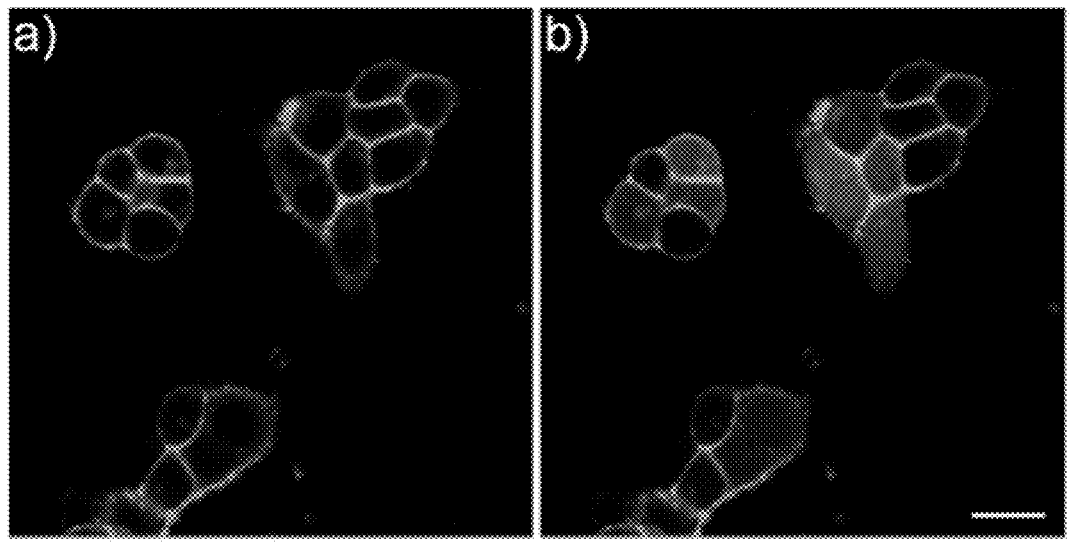
FIG. 8A-D shows characterization of monosulfo and disulfoVF dyes. (A-B) Confocal fluorescence images of dsVF2.2(OMe).Cl in HEK cells. Membrane-associated green fluorescence (panel a) shows clear membrane localization when compared with cytosolic mCherry (panel b). Scale bar is 20 μm. Membrane-localized dsVF2.2(OMe).Cl is voltage sensitive. (C) The fractional change in fluorescence is plotted vs. time for 100 ms hyper- and depolarizing steps (±100 mV, 20 mV increments) from a holding potential of −60 mV for a single HEK cells under whole-cell voltage-clamp mode. (D) A plot of % ΔF/F vs. final membrane potential (mV), summarizing data from 8 separate cells, reveals a voltage sensitivity of approximately 63% per 100 mV (±1.6%). Error bars are ±SEM.
Figures 8C, 8D:
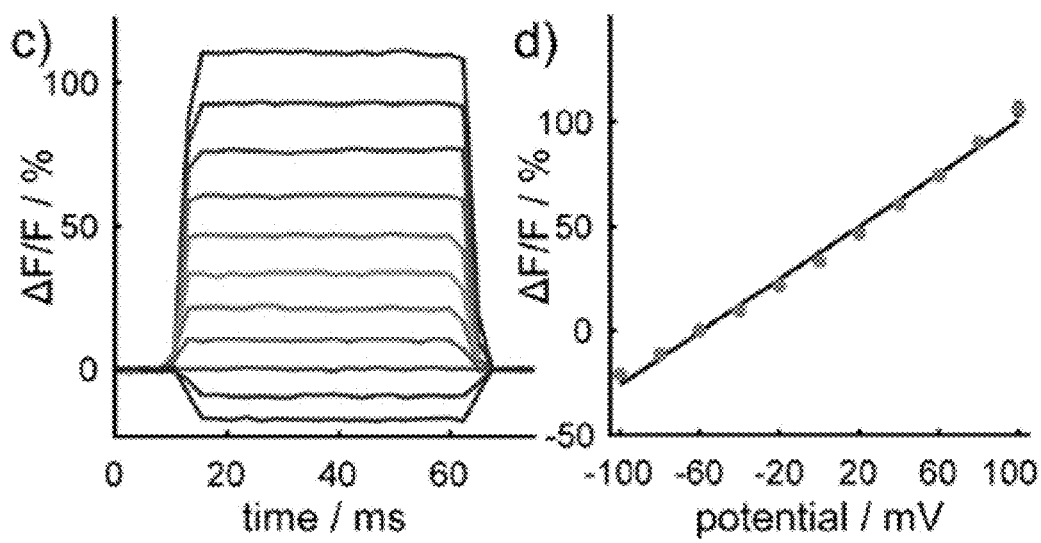
Figure 9A:
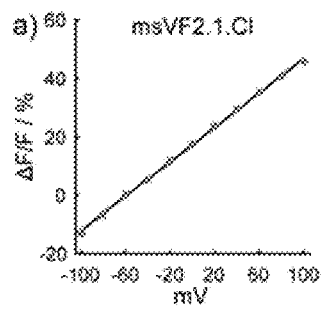
FIG. 9A-L shows voltage sensitivity of VF dyes in HEK cells. The fractional change in fluorescence is plotted vs. final membrane potential for 100 ms hyper- and depolarizing steps (±100 mV, 20 mV increments) from a holding potential of −60 mV for a single HEK cells under whole-cell voltage-clamp mode. Data are from between 3 and 8 individual cells for each point. Error bars are ±SEM.
Figure 9B:
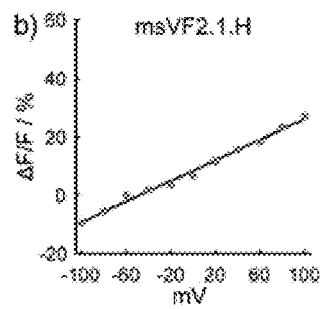
Figure 9C:
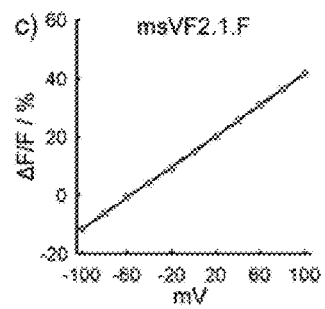
Figure 9D:
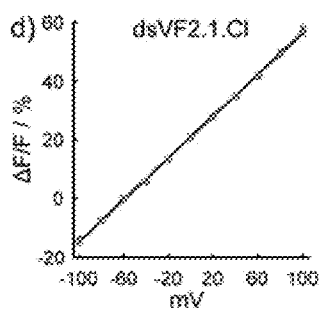
Figure 9E:
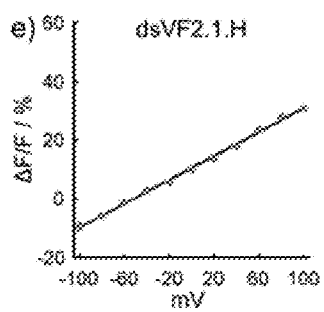
Figure 9F:
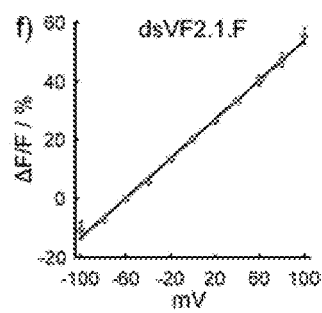
Figure 9G:
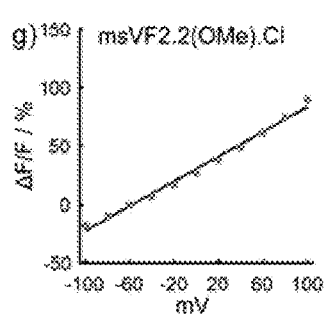
Figure 9H:
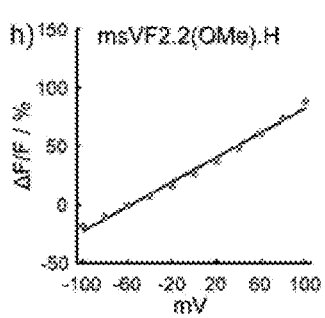
Figure 9I:
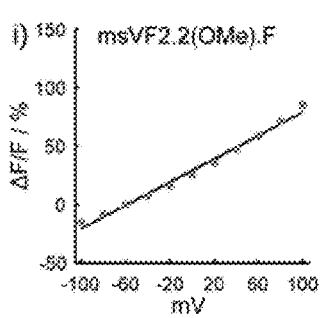
Figure 9J:
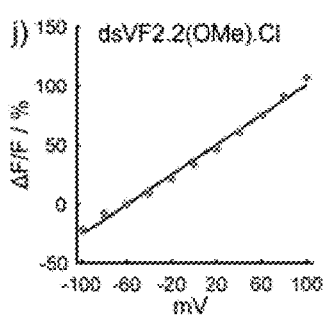
Figure 9K:
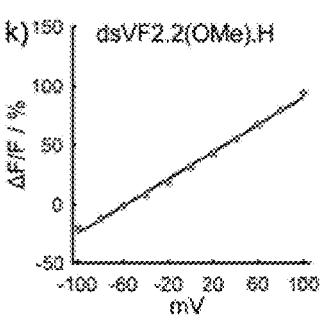
Figure 9L:
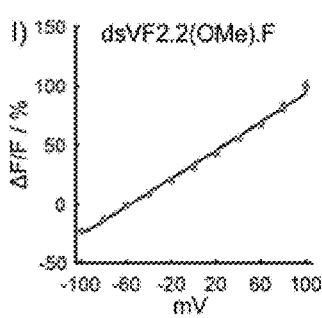

A total of 9 new dyes were made: 6 new dsVF dyes and 3 new msVF dyes. Both msVF and dsVF dyes display similar excitation and emission profiles to previously reported msVF dyes (Table 1, FIG. 7A-I), and all localized to the plasma membrane when applied to HEK293T cells via bath loading (FIG. 8a-b). In general, disulfonated fluorophores (8-10) and dsVF dyes (11b-16b) showed improved aqueous solubility relative to mono-sulfo derivatives (5-7, 11a-16a). Addition of a second sulfonate improved the aqueous solubility of fluorophore 8 2.3-fold relative to monosulfo 5, as determined either spectroscopically or gravimetrically. In the context of a full VF dye, a second sulfonate improved aqueous solubility by 22% for VF2.1.Cl and 55% for VF2.2(OMe).Cl (11a vs 11b; 12a vs 12b).

TABLE 1

Properties of mono- and disulfo VoltageFluor dyes

| Name | ID | R | R' | R" | $\Phi_{fl}{}^a$ | $\lambda_{abs}{}^a$ | $\lambda_{em}{}^a$ | ΔF/F (%)$^b$ | Improvement (%)$^c$ |
|---|---|---|---|---|---|---|---|---|---|
| msVF2.1.Cl | 11a | Cl | Me | H | 0.06 | 522 | 536 | 30 | — |
| dsVF2.1.Cl | 11b | Cl | Me | H | 0.08 | 520 | 539 | 36 | 21 |
| msVF2.2(OMe).Cl | 12a | Cl | Et | OMe | 0.06 | 518 | 534 | 53 | — |
| dsVF2.2(OMe).Cl | 12b | Cl | Et | OMe | 0.07 | 520 | 540 | 63 | 19 |
| msVF2.1.H | 13a | H | Me | H | 0.10 | 507 | 528 | 17 | — |
| dsVF2.1.H | 13b | H | Me | H | 0.14 | 509 | 540 | 20 | 17 |
| msVF2.2(OMe).H | 14a | H | Et | OMe | 0.08 | 508 | 530 | 53 | — |
| dsVF2.2(OMe).H | 14b | H | Et | OMe | 0.11 | 510 | 530 | 57 | 9 |
| msVF2.1.F | 15a | F | Me | H | 0.09 | 508 | 524 | 27 | — |
| dsVF2.1.F | 15b | F | Me | H | 0.13 | 507 | 529 | 33 | 25 |
| msVF2.2(OMe).F | 16a | F | Et | OMe | 0.06 | 505 | 524 | 49 | — |
| dsVF2.2(OMe).F | 16b | F | Et | OMe | 0.06 | 509 | 529 | 60 | 22 |

$^a$Measured in phosphate-buffered saline, pH 7.4 with 0.1% Triton X-100.
$^b$per 100 mV. Determined in HEK cells.
$^c$Relative to corresponding msVF.

To determine the voltage sensitivity of each of the dyes, whole-cell patch clamp electrophysiology was performed on HEK293T cells loaded with 200 nM VF (FIG. 8a-d). Depolarization of the cell membrane in the presence of VF dye results in a large increase of fluorescence, while hyperpolarization results in lower levels of fluorescence (FIG. 8c-d; FIG. 9). As an illustrative comparison, msVF2.2(OMe). Cl (12a) had a voltage sensitivity of approximately 53%±1% ΔF/F per 100 mV, which is comparable to msVF2.1(OMe). Cl, at 48% per 100 mV. The disulfoVF2.2(OMe). Cl (12b), when subjected to the same membrane depolarizations, had a voltage sensitivity of 63%±1% ΔF/F per 100 mV, representing a 19% improvement in voltage sensitivity over the monosulfonated VF analog, and the most sensitive VF dye to date.

Figure 10:
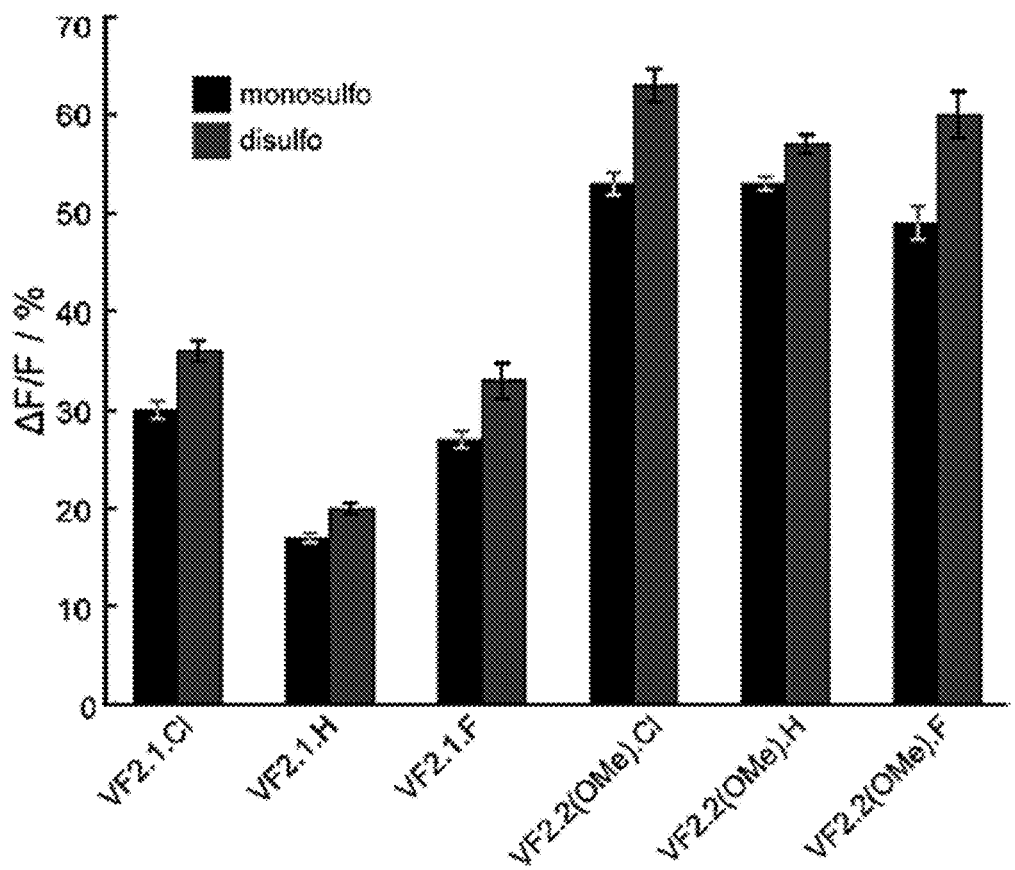
FIG. 10 shows a comparison of voltage sensitivity of monosulfo- and disulfo-VoltageFluor. Bars on the left represent msVF dyes and bars are the right represent dsVF dyes. Voltage sensitivity is reported as ΔF/F per 100 mV as measured in patch-clamped HEK cells. Values represent 3-8 independent determinations and error bars are ±SEM.
Figure 12:
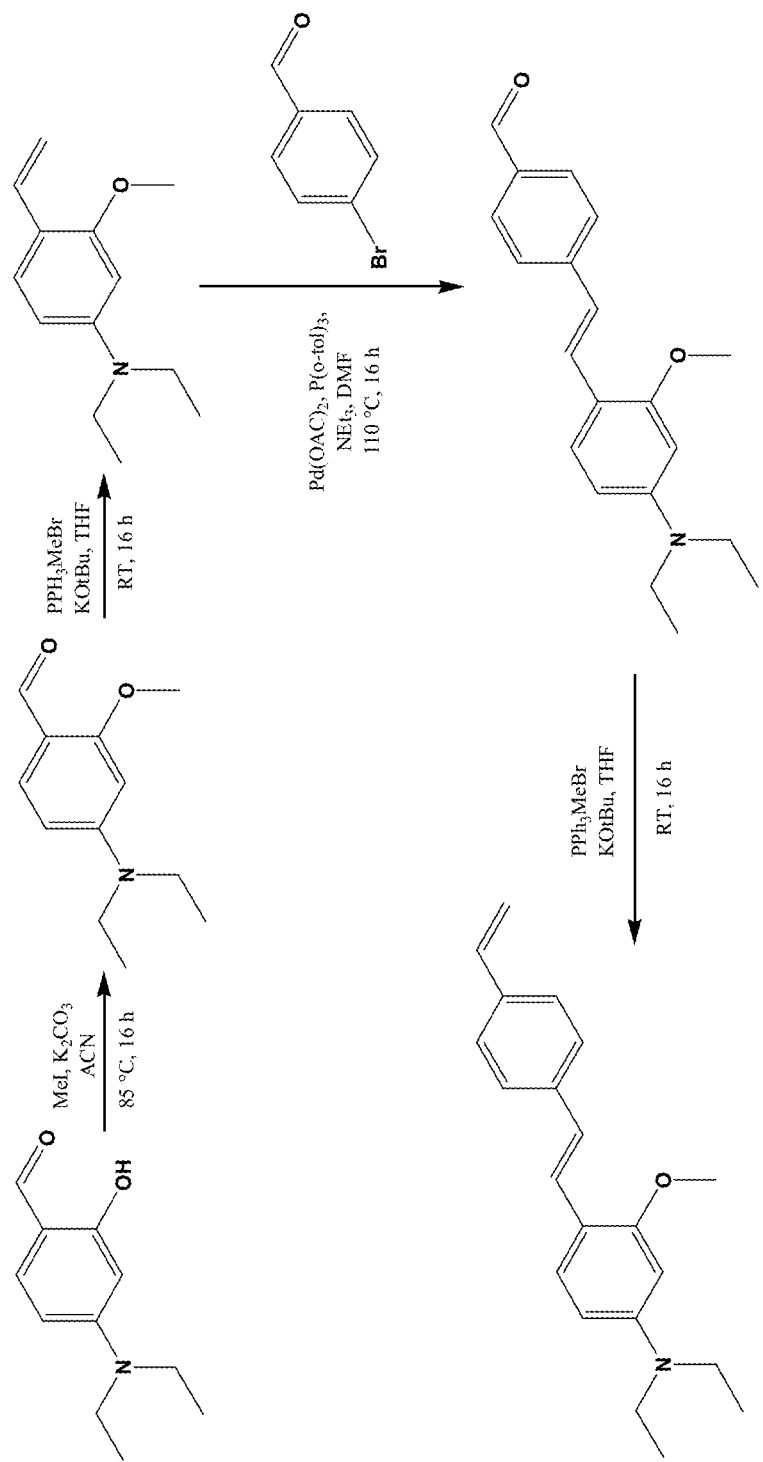
FIG. 12 presents exemplary schemes to synthesize diethyl-methoxy molecular wires.
Figure 13A:
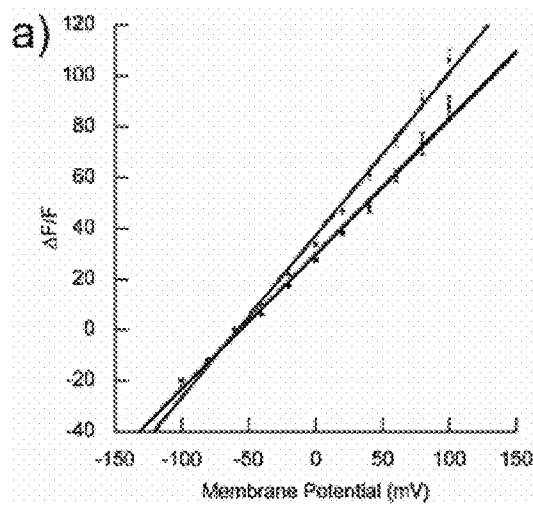
FIG. 13A-D presents a comparison of voltage sensitivities of VF2.2(OMe).Cl and disulfoVF2.2(OMe).Cl in HEK293T cells. (A) Percentage change in fluorescence (ΔF/F) vs. membrane potential (mV) for VF2.2(OMe).Cl and disulfoVF2.2(OMe). Cl. Error bars are SEM for n=5 experiments. (B) Widefield fluorescence image of HEK293T cells stained with 200 nM disulfoVF2.2(OMe).Cl for 15 minutes at 37° C. (C) Fractional change in disulfoVF2.2(OMe).Cl fluorescence (ΔF/F) vs. time in a HEK293T cell held under voltage clamp at −60 mV and then subjected to potentials ranging from +100 mV to −100 mV for 50 ms in 20 mV increments. Concatenated traces shown in (C) are representative of a single experiment. Scale bars are 20 μm. (D) Widefield fluorescence image of HEK293T cells stained with 200 nM VF2.2(OMe).Cl for 15 minutes at 37° C.
Figure 13B:
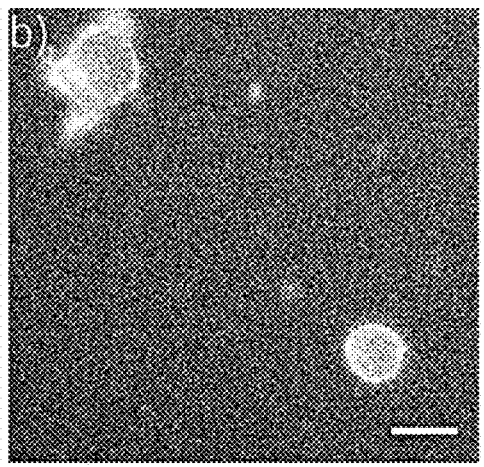
Figure 13C:
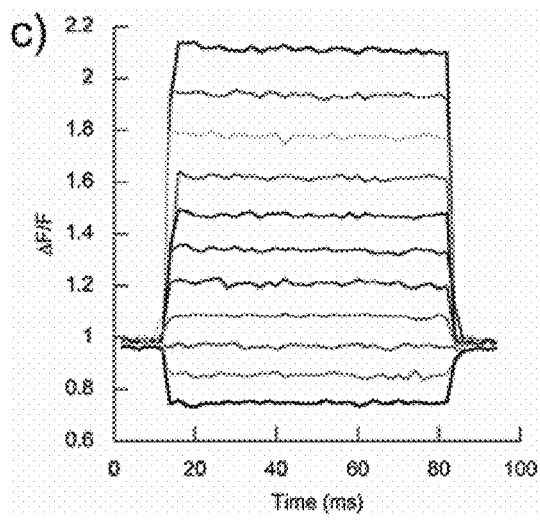
Figure 13D:
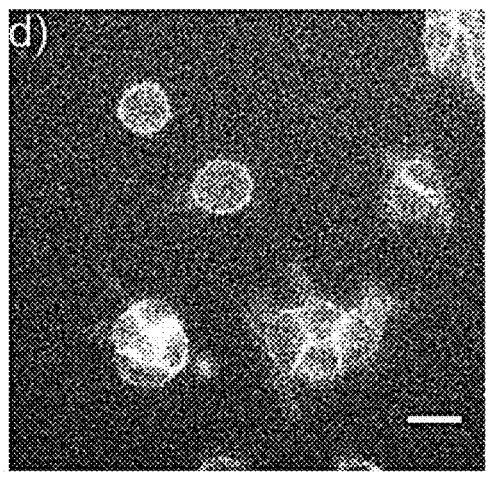

The voltage sensitivity for the remaining 10 VF dyes was determined using dual optical and electrophysiological recordings in HEK cells (3-8 separate cells per dye). All of the dyes—VF2.1.Cl (11), VF2.1.H (13), VF2.1.F (15), VF2.2(OMe).H (14), and VF2.2(OMe).F (16)—showed comparable improvements in voltage sensitivity when the second sulfonate group is added (Table 1, FIG. 10). In all cases, an increase in voltage sensitivity was observed upon transition to the dsVF dye. On average disulfoVF dyes show a 19%±2% increase in voltage sensitivity over its monosulfonated counterpart (Table 1). The experimentally determined average increase in voltage sensitivity of 19% matches well with the computationally predicted value of 16% and provides a validation both of the MD simulation methodology and the hypothesis that the relative orientation of the VF dye influences voltage sensitivity. The small discrepancy may arise from differences in the electronic nature of ms- vs dsVF dyes.

Due to its exceptional voltage sensitivity and good photostability compared to msVF2.2(OMe).Cl, it was expected that disulfoVF2.2(OMe).Cl would be well-suited to observing membrane potential changes in neurons. Cultured rat hippocampal neurons bathed in disulfoVF2.2(OMe).Cl showed bright membrane staining, as confirmed by confocal microscopy (FIG. 11a). dsVF2.2(OMe).Cl was also used to image neuronal activity in midbrain dopaminergic (mDA) neurons derived from cultured human pluripotent stem cells (hPSCs) in culture (FIG. 11b) using differentiation conditions adapted from previously established protocols. mDA neurons stained with dsVF2.2(OMe).Cl revealed distinct firing patterns (FIG. 11c,d). Functional analysis of human- or patient-derived differentiated neurons in a simple, non-invasive manner enabled by dsVF2.2(OMe).Cl can provide an important diagnostic tool alongside more conventional methods in ascertaining proper differentiation as well as in investigating human disease phenotypes.

A number of embodiments have been described herein. Nevertheless, it will be understood that various modifications may be made without departing from the spirit and scope of this disclosure. Accordingly, other embodiments are within the scope of the following claims.

What is claimed is:

1. A compound comprising the structure of Formula II:

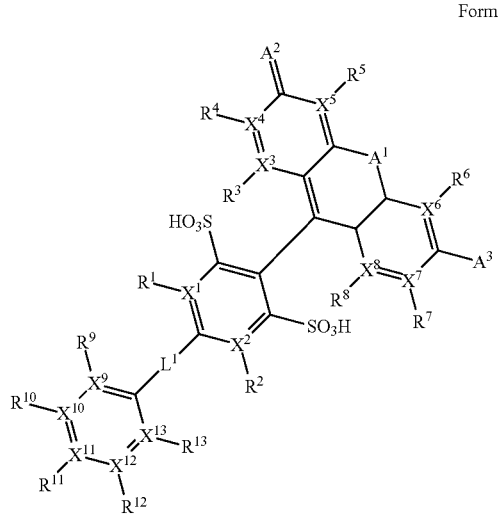

Formula II wherein, $L^1$ is selected from the group consisting of:

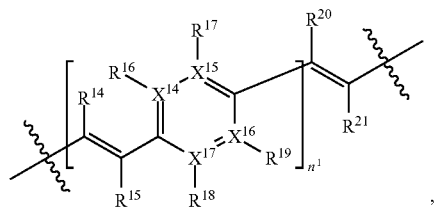

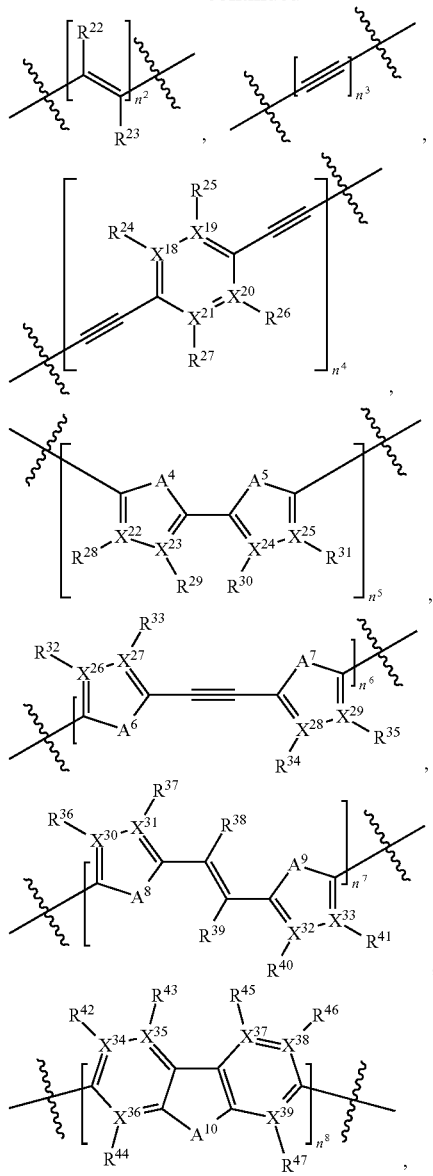

and any combination of the foregoing;

$A^1$, $A^4$-$A^{10}$ are each independently selected from $CH_2$, CHR', $CR'_2$, NH, O, S, Se, Te, $SiH_2$, SiHR', $SiR'_2$, $GeH_2$, GeHR', $GeR'_2$, $SnH_2$, SnHR', $SnR'_2$, $PbH_2$, PbHR', or $PbHR'_2$, wherein R' is selected from the group consisting of D, optionally substituted FG, optionally substituted ($C_1$-$C_{12}$)alkyl, optionally substituted ($C_1$-$C_{11}$)heteroalkyl, optionally substituted ($C_1$-$C_{12}$)alkenyl, optionally substituted ($C_1$-$C_{11}$)heteroalkenyl, optionally substituted ($C_1$-$C_{12}$)alkynyl, and optionally substituted ($C_1$-$C_{11}$)heteroalkynyl;

$A^2$ is selected from $NH_2$, S or O;

$A^3$ is selected from $NH_2$, OH, SH and methoxy;

$X^1$-$X^{39}$ are independently selected from N or C, wherein when an X group is an N, then the R group is absent; and $R^1$-$R^3$, $R^5$-$R^6$, $R^8$-$R^{10}$, $R^{12}$, and $R^{14}$-$R^{47}$ are independently selected from H, D, optionally substituted FG, optionally substituted ($C_1$-$C_{12}$)alkyl, optionally substituted ($C_2$-$C_{10}$)heteroalkyl, optionally substituted ($C_1$-

$C_{12}$)alkenyl, optionally substituted ($C_2$-$C_{10}$)heteroalkenyl, optionally substituted ($C_1$-$C_{12}$)alkynyl, optionally substituted ($C_2$-$C_{10}$)heteroalkynyl, optionally substituted ($C_3$-$C_{12}$)cycloalkyl, optionally substituted ($C_5$-$C_{12}$)cycloalkenyl, optionally substituted aryl, optionally substituted heterocycle, optionally substituted mixed ring system, wherein one or more adjacent R groups can be linked together to form one or more substituted rings selected from the group comprising ($C_3$-$C_{12}$)cycloalkyl, ($C_3$-$C_{12}$)cycloalkenyl, heterocycle, aryl, and mixed ring system;

wherein $R^4$ and $R^7$ are F or Cl;

$R^{11}$ is selected from $NH_2$, $NH(R^{50})$, $N(R^{50})_2$ wherein $R^{50}$ is a ($C_1$-$C_3$)alkyl;

wherein $R^{13}$ is an alkoxy; and $n^1$-$n^8$ are independently an integer selected from 0 to 10.

2. The compound of claim 1, wherein the compound comprises the structure of Formula III:

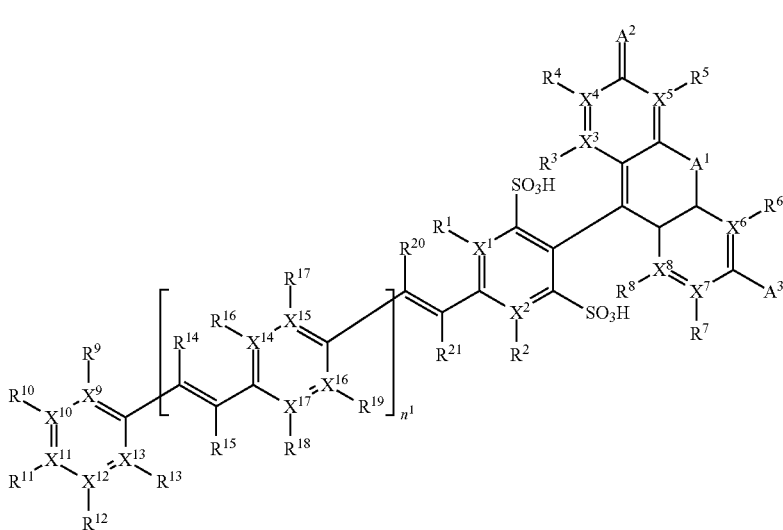

Formula III wherein,

A$^1$ is selected from CH$_2$, CHR', CR'$_2$, NH, O, S, Se, Te, SiH$_2$, SiHR', SiR'$_2$, GeH$_2$, GeHR', GeR'$_2$, SnH$_2$, SnHR', SnR'$_2$, PbH$_2$, PbHR', or PbHR'$_2$, wherein R' is selected from the group consisting of D, optionally substituted FG, optionally substituted ($C_1$-$C_{12}$)alkyl, optionally substituted ($C_2$-$C_{10}$)heteroalkyl, optionally substituted ($C_1$-$C_{12}$)alkenyl, optionally substituted ($C_2$-$C_{10}$)heteroalkenyl, optionally substituted ($C_1$-$C_{12}$)alkynyl, and optionally substituted ($C_2$-$C_{10}$)heteroalkynyl, A$^2$ is NH$_2$ or O;

A$^3$ is selected from NH$_2$, OH and methoxy;

X$^1$-X$^{17}$ are independently selected from N or C, wherein when an X group is an N, then the R group is absent; and R$^1$-R$^3$, R$^5$-R$^6$, R$^8$-R$^{10}$, R$^{12}$, and R$^{14}$-R$^{21}$ are independently selected from H, D, optionally substituted FG, optionally substituted ($C_1$-$C_{12}$)alkyl, optionally substituted ($C_2$-$C_{10}$)heteroalkyl, optionally substituted ($C_1$-$C_{12}$)alkenyl, optionally substituted ($C_2$-$C_{10}$)heteroalkenyl, optionally substituted ($C_1$-$C_{12}$)alkynyl, optionally substituted ($C_2$-$C_{10}$)heteroalkynyl, optionally substituted ($C_3$-$C_{12}$)cycloalkyl, optionally substituted ($C_5$-$C_{12}$)cycloalkenyl, optionally substituted aryl, optionally substituted heterocycle, optionally substituted mixed ring system, wherein one or more adjacent R groups can be linked together to form one or more substituted rings selected from the group comprising ($C_3$-$C_{12}$)cycloalkyl, ($C_3$-$C_{12}$)cycloalkenyl, heterocycle, aryl, and mixed ring system;

wherein $R^4$ and $R^7$ are F or Cl;

$R^{11}$ is selected from $NH_2$, $NH(R^{50})$, $N(R^{50})_2$ wherein $R^{50}$ is a ($C_1$-$C_3$)alkyl;

wherein $R^{13}$ is an alkoxy; and $n^1$ is an integer selected from 0 to 10.

3. The compound of claim 2, wherein the compound comprises the structure of Formula III(a):

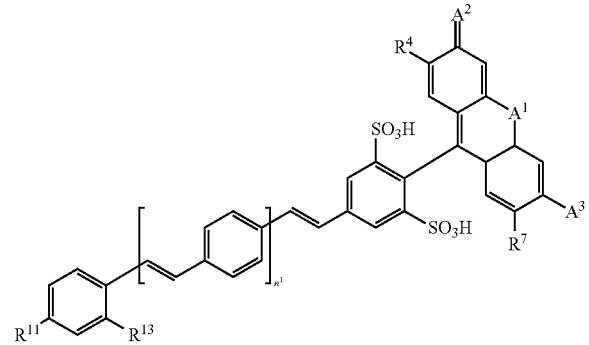

Formula III(a)

wherein,

A$^1$ is selected from CH$_2$, CHR', CR'$_2$, NH, O, S, Se, Te, SiH$_2$, SiHR', SiR'$_2$, GeH$_2$, GeHR', GeR'$_2$, SnH$_2$, SnHR', SnR'$_2$, PbH$_2$, PbHR', or PbHR'$_2$, wherein R' is selected from the group consisting of D, optionally substituted FG, optionally substituted ($C_1$-$C_6$)alkyl, optionally substituted ($C_2$-$C_5$)heteroalkyl, optionally substituted ($C_1$-$C_6$)alkenyl, optionally substituted ($C_2$-

$C_5$)heteroalkenyl, optionally substituted ($C_1$-$C_6$)alkynyl, and optionally substituted ($C_2$-$C_5$)heteroalkynyl,
$A^2$ is $NH_2$ or O;
$A^3$ is $NH_2$ or OH;
$R^4$ and $R^7$ are independently F, and/or Cl;
$R^{11}$ is selected from $NH_2$, $NH(R^{50})$, $N(R^{50})_2$, wherein $R^{50}$ is a ($C_1$-$C_3$)alkyl;
$R^{13}$ is an alkoxy; and
$n^1$ is an integer selected from 0 to 5.

4. The compound of claim 3, wherein the compound comprises the structure of Formula III(b):

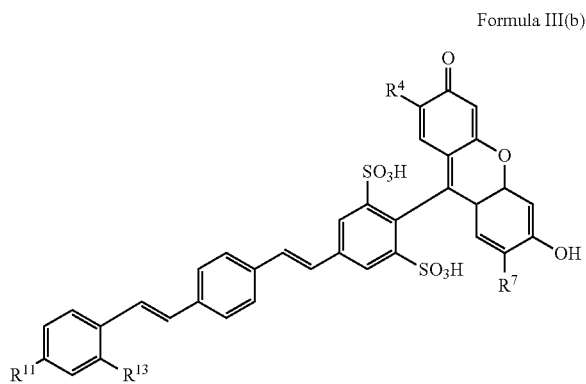

Formula III(b)

wherein,
$R^4$ and $R^7$ are independently F, and/or Cl;
$R^{11}$ is selected from $NH_2$, $NH(R^{50})$, $N(R^{50})_2$, wherein $R^{50}$ is a ($C_1$-$C_3$)alkyl; and
$R^{13}$ is a methoxy.

5. The compound of claim 1, wherein the compound has one or more of the following characteristics:
the compound is water soluble;
the compound exhibits a tilt angle from 0° to 20°;
the compound exhibits a voltage sensitivity of 63% ΔF/F per 100 mV or greater; and
the compound can undergo photoinduced electron transfer.

6. The compound of claim 5, wherein the compound is characterized by being water soluble; exhibits a tilt angle of about 0°; exhibits a voltage sensitivity of 63% ΔF/F per 100 mV or greater; and can undergo photoinduced electron transfer.

7. A method to image cells, comprising:
contacting the cell with a compound of claim 1;
illuminating the cells with light having a first wavelength;
imaging the cells by detecting light having a second wavelength,
wherein the first wavelength and second wavelength of light have different wavelengths, and wherein the light having the second wavelength is in the far red to near infrared region.

8. The method of claim 7, wherein the method further comprises:
contacting the cells with one or more additional optogenetic tools; and
imaging the cells be detecting light emissions at one or more additional wavelengths.

9. The method of claim 8, wherein the one or more optogenetic tools are selected from GFP, $Ca^{2+}$ indicators, voltage sensors based on cpGFP, and ChannelRhodopsin2 (ChR2).

10. A method to measure changes in membrane potential in an excitable cell comprising:
contacting the excitable cell with a compound of claim 1;
stimulating the cell to evoke action potentials; and
measuring action potential firing by optical or electrical sampling.

11. The method of claim 10, wherein the optical sampling is measured using an electron multiplying charge couple device.

12. The method of claim 11, wherein the excitable cell is stimulated using a whole-cell current clamp or by field stimulation.

13. The method of claim 10, wherein the excitable cell is a neuron, cardiomyocyte, myocyte, or a secretory cell.

14. The method of claim 13, wherein the method interrogates membrane potentials of a neuron.

15. A kit comprising:
a plurality of compartments which comprise a compound of claim 1 in a buffered solution, or a concentrated solution.

* * * * *